(12) United States Patent
Kandel et al.

(10) Patent No.: US 7,810,928 B2
(45) Date of Patent: Oct. 12, 2010

(54) EVALUATING PUPILLARY RESPONSES TO LIGHT STIMULI

(75) Inventors: Gillray L. Kandel, Troy, NY (US); Aaron S. Cohen, Troy, NY (US)

(73) Assignee: Konan Medical USA, Inc., Irvine, CA (US)

( * ) Notice: Subject to any disclaimer, the term of this patent is extended or adjusted under 35 U.S.C. 154(b) by 37 days.

(21) Appl. No.: 12/393,150

(22) Filed: Feb. 26, 2009

(65) Prior Publication Data

US 2009/0213329 A1 Aug. 27, 2009

Related U.S. Application Data

(60) Provisional application No. 61/031,494, filed on Feb. 26, 2008, provisional application No. 61/097,048, filed on Sep. 15, 2008.

(51) Int. Cl.
*A61B 3/10* (2006.01)
(52) U.S. Cl. .................. 351/221; 351/205; 351/246
(58) Field of Classification Search .................. 351/221, 351/206, 209, 210, 211, 212, 246, 205
See application file for complete search history.

(56) References Cited

U.S. PATENT DOCUMENTS 2,573,464 A 10/1951 Lowenstein et al.

(Continued)

FOREIGN PATENT DOCUMENTS

JP 404317624 A 11/1992

(Continued)

OTHER PUBLICATIONS

EP03788506; Supplementary Partial European Search Report; Mar. 2, 2009; 4 pages.

(Continued)

*Primary Examiner*—Hung X Dang
(74) *Attorney, Agent, or Firm*—John W. LaBatt; Hoffman Warnick LLC

(57) ABSTRACT

Solutions for evaluating the pupillary responses of a patient are disclosed. An illustrative method includes alternately exposing a first eye and a second eye of the patient to light stimulation in successive intervals, the light stimulation provided by at least one light source controlled by at least one computing device; concurrently capturing, with at least one image device controlled by the at least one computing device, image data of the first eye and the second eye during the exposing; and using the at least one computing device to perform the following: determine a center point of the first eye within the image data of the first eye and a center point of the second eye within the image data of the second eye; obtain image data of a first half of the first eye having an edge defined by a line of pixels intersecting the determined center point of the first eye; obtain image data of a second half of the second eye, the second half of the second eye opposing the first half of the first eye and having an edge defined by a line of pixels intersecting the determined center point of the second eye; create a composite image including the image data of the first half of the first eye and the image data of the second half of the second eye; and provide the composite image for evaluation.

20 Claims, 18 Drawing Sheets

U.S. PATENT DOCUMENTS

| | | | |
|---|---|---|---|
| 3,036,568 | A | 5/1962 | Stark |
| 3,533,683 | A | 10/1970 | Stark et al. |
| 3,533,684 | A | 10/1970 | Stark et al. |
| 3,639,041 | A | 2/1972 | Cornsweet |
| 3,770,342 | A | 11/1973 | Dudragne |
| 3,966,310 | A | 6/1976 | Larson |
| 4,012,128 | A | 3/1977 | Regan |
| 4,208,107 | A | 6/1980 | Oharek |
| 4,651,257 | A | 3/1987 | Gehly |
| 4,755,043 | A | 7/1988 | Carter |
| 4,822,162 | A | 4/1989 | Richardson et al. |
| 4,850,691 | A | 7/1989 | Gardner et al. |
| 5,042,937 | A | 8/1991 | Cornsweet |
| 5,065,767 | A | 11/1991 | Maddess |
| 5,187,506 | A | 2/1993 | Carter |
| 5,237,349 | A | 8/1993 | Burckhardt |
| 5,295,495 | A | 3/1994 | Maddess |
| 5,490,098 | A | 2/1996 | Kardon |
| 5,506,633 | A | 4/1996 | Sperling |
| 5,539,482 | A | 7/1996 | James et al. |
| 5,609,159 | A | 3/1997 | Kandel et al. |
| 5,632,282 | A | 5/1997 | Hay et al. |
| 5,646,709 | A | 7/1997 | Carter |
| 5,661,538 | A | 8/1997 | Carter |
| 5,784,145 | A | 7/1998 | Ghodse et al. |
| 5,883,691 | A | 3/1999 | Ishikawa et al. |
| 5,892,568 | A | 4/1999 | Carter |
| 5,912,723 | A | 6/1999 | Maddess |
| 5,956,125 | A | 9/1999 | Rosse et al. |
| 6,022,109 | A * | 2/2000 | Dal Santo .................. 351/221 |
| 6,086,206 | A | 7/2000 | Sutter |
| 6,162,186 | A | 12/2000 | Scinto et al. |
| 6,315,414 | B1 | 11/2001 | Maddess et al. |
| 6,382,792 | B1 | 5/2002 | Khoury |
| 6,497,483 | B2 | 12/2002 | Frey et al. |
| 6,561,648 | B2 | 5/2003 | Thomas |
| 6,644,810 | B1 | 11/2003 | Ulbers |
| 6,669,651 | B1 | 12/2003 | Fukushima et al. |
| 6,702,757 | B2 | 3/2004 | Fukushima et al. |
| 6,820,979 | B1 | 11/2004 | Stark et al. |
| 6,879,443 | B2 | 4/2005 | Spitzer et al. |
| 7,006,863 | B2 | 2/2006 | Maddess et al. |
| 7,204,590 | B1 * | 4/2007 | Lenoir ........................ 351/205 |
| 7,334,895 | B2 * | 2/2008 | Kandel et al. ............... 351/221 |
| 7,452,079 | B1 * | 11/2008 | Lenoir ........................ 351/205 |
| 7,488,073 | B2 * | 2/2009 | Kandel et al. ............... 351/221 |
| 2002/0024633 | A1 | 2/2002 | Kim et al. |
| 2008/0198330 | A1 | 8/2008 | Taylor |

FOREIGN PATENT DOCUMENTS

| | | |
|---|---|---|
| JP | 2002034926 A | 2/2002 |
| WO | 2006032920 A2 | 3/2006 |

OTHER PUBLICATIONS

U.S. Appl. No. 61/097,048, filed Sep. 15, 2008.
U.S. Appl. No. 61/031,494, filed Feb. 26, 2008.
U.S. Appl. No. 10/641,435, Notice of Allowance, May, 11, 2007.
U.S Appl. No. 10/641,435, Office Action 2, Jun. 22, 2006.
U.S. Appl. No. 10/641,435, Office Action 1, Apr. 6, 2006.
PCT/US03/25550, Search Report, Feb. 11, 2004.
Riggs, et al., "Electrical Responses of the Human Eye to Changes in Wavelength of the Stimulating Light", Journal of the Optical Society of America, Nov. 1996, vol. 56, No. 11, pp. 1621-1625.
Johnson, "The Relative Afferent Pupillary Defect and a Novel Method of Fusion Recovery with the Worth 4-Dot Test", American Medical Association, Archives of Ophthalmology, Feb. 1996, vol. 114.
Maxner, "Pupil Disorders", Neuro-ophthalmology Course, Camp Hill Medical Centre, Dalhousie University, Halifax, Nova Scotia, Jun. 19, 1991, pp. 1-12.
Thompson, et al., "Asymmetry of Pupillomotor Input", Neuro-ophthalmology Unit, Departments of Ophthalmology and Neurology, University of Iowa, 1991.
Adams et al., "Clinical Measures of Central Vision Function in Glaucoma and Ocular Hypertension", Archives of Ophthalmology, Jun. 1987, vol. 105, pp. 782-787.
Adams et al., "New Clinical Color Threshold Test for Eye Disease", American Journal of Optometry and Physiological Optics, Jan. 1987, vol. 64, No. 1, pp. 29-37.
Young, et al., "Screening of Red-Green Color-Deficient Observers Using the Chromatic Pupillary Response", Clinical Vision Science, 1987, vol. 2, No. 2, pp. 117-122.
Young, et al., "Pupil Responses to Foveal Exchange of Monochromatic Lights", Optical Society of America, Jun. 1980, vol. 70, No. 6, pp. 697-706.
Wilhelm et al., "Clinical Application of Pupillography", Journal of Neuro-Ophthalmology, vol. 23 (1), Mar. 2003, pp. 42-49, Copyright 2003 Lippincott Williams & Wilkins.

* cited by examiner

RIGHT EYE VS. RIGHT EYE

| | B | A | P | N | L | S | J | O | Y |
|---|---|---|---|---|---|---|---|---|---|
| B | 1 | 0.425 | | | | | | | |
| A | | 1 | 0.581 | | | | 0.498 | | |
| P | | | 1 | | | | 0.481 | | |
| N | | | | 1 | | | | | |
| L | | | | | 1 | | | | |
| S | | | | | | 1 | | | |
| J | | | | | | | 1 | | 0.417 |
| O | | | | | | | | 1 | 0.504 |
| Y | | | | | | | | | 1 |

FIG. 8A

LEFT EYE VS. LEFT EYE

| | B | A | P | N | L | S | J | O | Y |
|---|---|---|---|---|---|---|---|---|---|
| B | 1 | | | | | 0.604 | | | |
| A | | 1 | | | | 0.657 | | 0.462 | |
| P | | | 1 | | | | | | |
| N | | | | 1 | | | | | |
| L | | | | | 1 | | | | |
| S | | | | | | 1 | | | |
| J | | | | | | | 1 | | |
| O | | | | | | | | 1 | |
| Y | | | | | | | | | 1 |

FIG. 8B

RIGHT EYE (PATIENTS ON SIDE) VS. LEFT EYE (PATIENTS ON TOP)

| | B | A | P | N | L | S | J | O | Y |
|---|---|---|---|---|---|---|---|---|---|
| B | 0.578 | | | | | | | | 0.420 |
| A | | | 0.736 | | | | | | |
| P | | | 0.817 | | | | | | |
| N | | | | | 0.477 | | | | |
| L | | | | | | | | | |
| S | | 0.487 | | 0.494 | | 0.576 | | | |
| J | | | 0.695 | | | | 0.795 | | |
| O | | | | | | | | | |
| Y | | | | | | | | | 0.827 |

FIG. 8C

*ONLY POSITIVE INERCORRELATIONS REACHING P=0.055 ON A ONE TAILED TEST ARE SHOWN

EVALUATING PUPILLARY RESPONSES TO LIGHT STIMULI

REFERENCE TO PRIOR APPLICATIONS

The current application claims the benefit of U.S. Provisional Application No. 61/031,494, titled "Method, System and Device for Detecting Ocular Dysfunctions", which was filed on 26 Feb. 2008, and U.S. Provisional Application No. 61/097,048, titled "Automated Swinging Flashlight Test", which was filed on 15 Sep. 2008, both of which are hereby incorporated by reference.

BACKGROUND OF THE INVENTION

1. Technical Field

The invention generally relates to a solution for evaluating pupillary responses to light stimuli. More particularly, the invention provides a solution for exposing one or both eyes to a series of light flashes and measuring the direct and/or consensual pupillary reflexes that can be used to detect the presence of various dysfunctions and/or disorders.

2. Background Art

During eye examinations, the pupillary reflexes of a patient are often monitored to determine the presence of various ocular dysfunctions. The presence of one or more ocular dysfunctions can signal that the patient suffers from an ocular disorder such as optic neuropathy, other pathology of the ocular pathways between the photoreceptors of the retina and brain, opacification of the ocular media, or conditions that impact the transmission of light through the ocular media. A common objective visual functional test for the detection of such visual dysfunctions is the "Swinging Flashlight Test" (SFT). For the SFT, a handheld, very bright light source is shined first into one eye of the patient and then into the other eye, in a pendular fashion with a period of one to two seconds. While this is being done, the examiner will observe the reflexes of the patient's pupils. A detection of a positive sign is made based on the observed reflexes.

For example, if the light is shined into an eye that has an optic nerve conduction defect, while the other eye does not, the pupil of the eye with the defect will contract to a lesser degree than will the pupil of the eye without the defect when that eye is stimulated with the same light. Similarly, if both eyes have a defect, one having a greater defect than the other, the light being shined into the eye with the greater defective optic nerve will evoke a lesser pupillary contraction of both pupils than would the same light shown into the eye with the lesser optic nerve defect, thus yielding the sign of a Relative Afferent Pupillary Defect (RAPD). Moreover, in the presence of a RAPD, when the light is alternated every few seconds between the two eyes, these differences in pupillary reflexes to the same bright light shined into the two eyes can give rise to an "illusion" that shining the same bright light into the eye with the greater defect caused its pupil to dilate (or expand), a so called Marcus-Gunn pupil.

Clinical methods currently exist to quantify RAPD by a nullifying exercise in which the light entering the more sensitive eye is reduced by placing Neutral Density (ND) filters, sbisa bars, or crossed polarizing filters between the eye and the light in increasing grades until the positive sign of pupillary escape is no longer apparent. The intensity of the filter used to reach this nullification can be viewed as a quantitative measurement of the difference in light sensitivity between the two eyes, and is usually expressed in Log units of ND. Generally, RAPDs of a magnitude less than 0.3 Log units are not measurable with this procedure, possibly owing the limitations of the examiner being able to observe small changes in pupil size of both eyes simultaneously. Often, 0.3 Log units is the minimum magnitude ND filter available to clinicians.

The SFT is an example of an objective functional test of the visual system that depends upon differences in pupillary reflexes to infer the presence of an ocular dysfunction. The presence of an ocular dysfunction can indicate an ocular disorder (i.e., disease or pathology). However, the SFT has numerous drawbacks. In particular, it lacks specificity for any one ocular disorder whether of neurological or transmissive origin. For example, it can be positive in unilateral dense cataracts, in certain unilateral retinal disorders, in anisocoria, as well as in significant asymmetric glaucoma. A clinician performing the SFT cannot tell which ocular disorder is present based solely on the pupillary reflexes. Moreover, the SFT lacks sensitivity due to the manner in which the differences between the direct and consensual reflexes are observed. For example, the clinician cannot observe the pupils of both eyes simultaneously, but must visualize the reflex of one pupil first and then visualize the reflex of the other pupil moments later. As a result, small differences in reflexes may go unnoticed. The unaided observation makes this comparative judgment subject to significant error and makes the detection of small differences in reflexes between the two eyes especially problematic. Because the SFT relies on the examiner's naked eye to detect and diagnose ocular dysfunctions, it lacks practical utility. Moreover, by depending on a single bright light, the SFT stimulates the visual system in an indiscriminate manner. As a result, this manner of evoking the pupils' reflexes is lacking in both sensitivity and specificity.

Further, several observations have been made concerning the ocular disorder glaucoma, thought to be a form of optic neuropathy. First, patients with glaucoma and patients present with symptoms of glaucoma display a significant degree of dyschromatopsia, i.e., deficiencies in color discrimination. Second, patients with asymmetric glaucoma, as measured by visual field loss and cup-disc ratios, manifest gross afferent pupillary defects to a greater extent than do patients without glaucoma. Third, a consensual pupillary reflex can be induced by the interchange of equally luminous, heterochromatic members of a pair of lights shined into the patient's contralateral eye. This finding indicates that chromatic differences in stimuli activate pupillary reflexes via stimulation of different cell populations, and that such activation is independent of the luminosity change thought to be the primary basis of pupillary reflex activation in the SFT.

Attempts have been made to solve these problems by implementing systems and devices for measuring pupillary reflexes to light stimuli. Such devices generally implement a system for exposing a patient's eyes to stimuli and then measuring the pupillary reaction thereof. In particular, the goal is to intentionally induce a pupillary reflex and then measure the reflex using various means. Because dimensional changes in the pupil's movements can often be minuscule, the comparison to a range of "normal" reactions obtained from different patients can lack accuracy. Without an appropriate validation procedure, this could lead to a false diagnosis of a disorder that is not present, a failure to diagnose a disorder that is present, or a failure to distinguish between two ocular diseases. Furthermore, if the examiner is seeking specific information, for example, about the afferent optic nerve pathology of a patient, efferent deficiencies may significantly confound the interpretation of such information.

SUMMARY OF THE INVENTION

The invention provides a solution for evaluating pupillary responses to light stimuli. In particular, a first aspect of the invention provides a method of evaluating the pupillary responses of a patient, the method comprising: alternately exposing a first eye and a second eye of the patient to light stimulation in successive intervals, the light stimulation provided by at least one light source controlled by at least one computing device; concurrently capturing, with at least one image device controlled by the at least one computing device, image data of the first eye and the second eye during the exposing; and using the at least one computing device to perform the following: determine a center point of the first eye within the image data of the first eye and a center point of the second eye within the image data of the second eye; obtain image data of a first half of the first eye having an edge defined by a line of pixels intersecting the determined center point of the first eye; obtain image data of a second half of the second eye, the second half of the second eye opposing the first half of the first eye and having an edge defined by a line of pixels intersecting the determined center point of the second eye; create a composite image including the image data of the first half of the first eye and the image data of the second half of the second eye; and provide the composite image for evaluation.

A second aspect of the invention provides a system for evaluating the pupillary responses of a patient, the system comprising: at least one light source for alternately exposing a first eye and a second eye, respectively, to light stimulation in successive intervals; at least one image capturing device for concurrently capturing image data of the first eye and the second eye, respectively; an image manipulation system including: a component configured to determine a center point of the first eye within the image data of the first eye and a center point of the second eye within the image data of the second eye; a component configured to obtain image data of a first half of the first eye having an edge defined by a line of pixels intersecting the determined center point of the first eye; a component configured to obtain image data of a second half of the second eye, the second half of the second eye opposing the first half of the first eye and having an edge defined by a line of pixels intersecting the determined center point of the second eye; a component configured to create a composite image including the image data of the first half of the first eye and the image data of the second half of the second eye; and a component configured to provide the composite image for evaluation.

A third aspect of the invention provides a method of evaluating the pupillary responses of a patient, the method comprising: alternately exposing a first eye and a second eye of the patient to light stimulation in successive intervals, the light stimulation provided by light sources controlled by at least one computing device; concurrently capturing, with an image device controlled by the at least one computing device, image data of the first eye and the second eye during the exposing; and using the at least one computing device to perform the following: convert the image data of the first eye and the second eye to binarized images of the first eye and the second eye that separate an pupil portion from a non-pupil portion; determine a center point of the first eye within the image data of the first eye and a center point of the second eye within the image data of the second eye; obtain image data of a first half of the first eye having an edge defined by a line of pixels intersecting the determined center point of the first eye; obtain image data of a second half of the second eye, the second half of the second eye opposing the first half of the first eye and having an edge defined by a line of pixels intersecting the determined center point of the second eye; create a composite image including the image data of the first half of the first eye and the image data of the second half of the second eye; and provide the composite image for evaluation.

A fourth aspect of the invention provides a device for detecting an ocular dysfunction, comprising: a first eye scope for exposing a first eye to a series of flashes and detecting a pupillary reflex of the first eye for each flash, the first eye scope having an ocular aperture, a light aperture, and a monitoring aperture; a second eye scope for detecting a pupillary reflex of a second eye for each flash, the second eye scope having an ocular aperture and a monitoring aperture; and a first light source for generating the series of flashes through the light aperture, wherein each flash in the series of flashes varies by at least one of: chromatically, location in the visual field, and luminosity from the other flashes in the series of flashes.

A fifth aspect of the invention provides a device for detecting ocular dysfunctions that comprises: (1) a light emitting sphere having: (a) an exit port; (b) an outer portion positioned along a periphery of the exit port, wherein the outer portion has a light source disposed thereon; and (c) a reflective well portion, wherein light emitted from the light source shines from the outer portion to the reflective well portion, and wherein the light reflects off the reflective well portion and exits the light emitting sphere through the exit port as a single beam of light.

The illustrative aspects of the invention are designed to solve the problems herein described and other problems not discussed, which are discoverable by a skilled artisan.

BRIEF DESCRIPTION OF THE DRAWINGS

These and other features of this invention will be more readily understood from the following detailed description of the various aspects of the invention taken in conjunction with the accompanying drawings in which:

FIGS. 8A-8C show an illustrative set of inter-correlation matrices constructed according to yet another aspect of the invention;

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As stated above, the invention provides a solution for evaluating pupillary responses to light stimuli. The solution can include, for example, methods and/or systems that capture data about a patient's response to light stimuli. The solution can further include methods and/or systems that manipulate the captured data in order to evaluate the patient's response. In particular, a first eye is exposed to a series of flashes. Each flash can include substantially "white" light, or each flash can vary chromatically from the other flashes in the series. Pupillary reflexes for both eyes are measured during the exposures. The pupillary reflexes can be evaluated to determine if an ocular dysfunction is present. In one embodiment, both eyes are alternately exposed to the same series of flashes. Further, additional series of flashes that vary by location in the visual field and/or luminosity (i.e., brightness) can be incorporated and evaluated.

In an embodiment, the invention can target different visual functions and cell populations by incorporating series of flashes that vary chromatically, by luminosity, and/or by location in the visual field. Each flash comprises a beam of light having a short time duration. In one embodiment, each flash is terminated before the release (escape) phase of the pupillary reflex has begun. This release phase can take, for example, approximately 0.6 seconds. Using flashes having short time durations allows for a substantial increase in the number of distinct afferent and efferent reflex pathways that can be probed as compared with SFT. Probing a larger number of pathways allows for a highly discriminative and sensitive measure of any optic neuropathology that can manifest in any of the different conductive ocular pathway pathologies. It further allows for a separate assessment of efferent pathology. The data provided by the series of flashes can be processed to detect afferent optic nerve or efferent pupillary asymmetry. Further, the data can provide a direction sensitive measurement of pupillary reflexes in both eyes. Consequently, the invention can provide sufficiently sensitive measurements to evaluate asymmetric precursory manifestations (i.e., ocular dysfunctions) of ocular disorders that are bilateral in nature. For example, ocular dysfunctions present in disorders such as the glaucoma group of eye diseases, optic neuritis, retinal pathologies, etc. can be detected using the present invention.

Figure 1A:
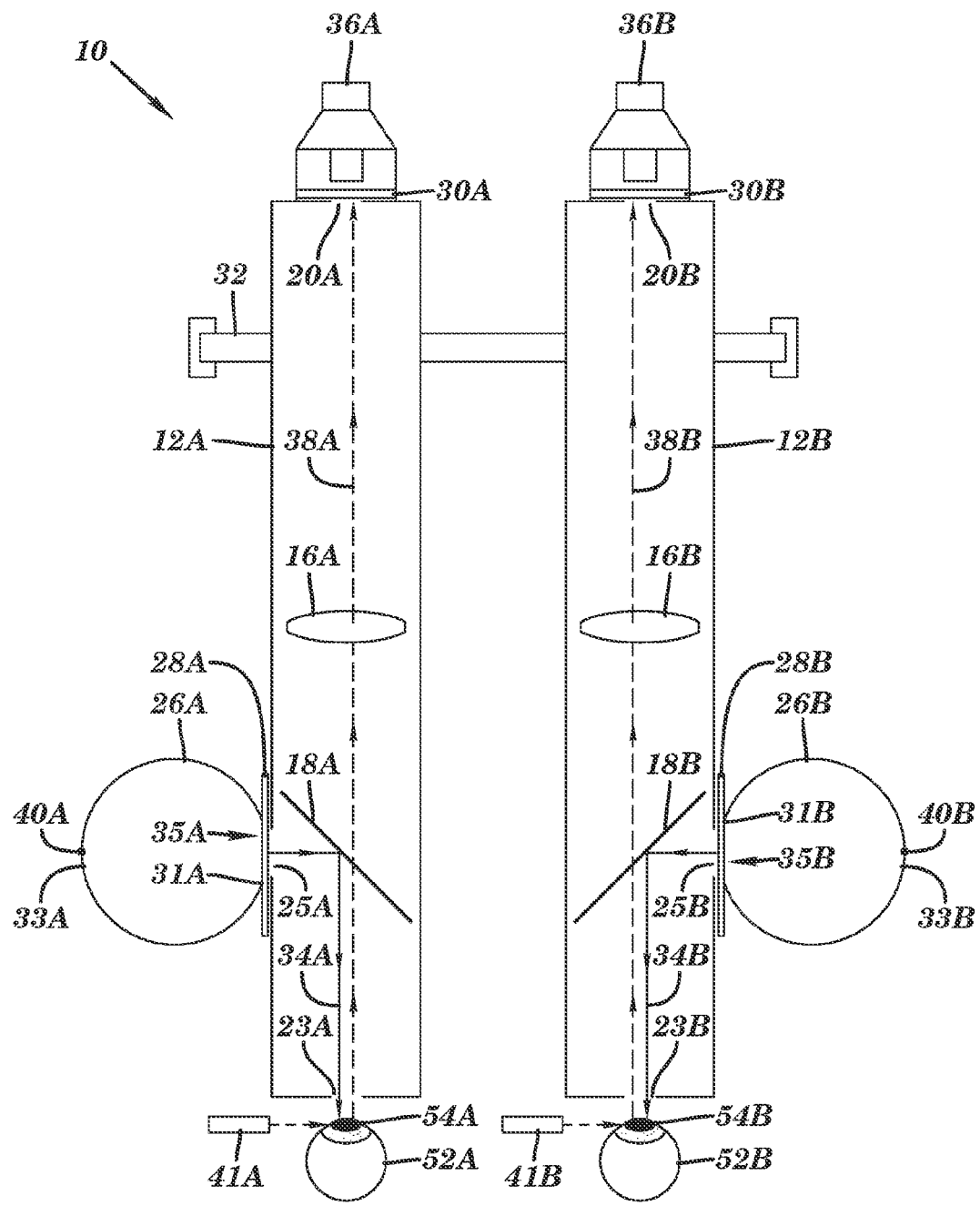
FIG. 1A is a top view of a device according to one aspect of the invention.
Figure 1B:
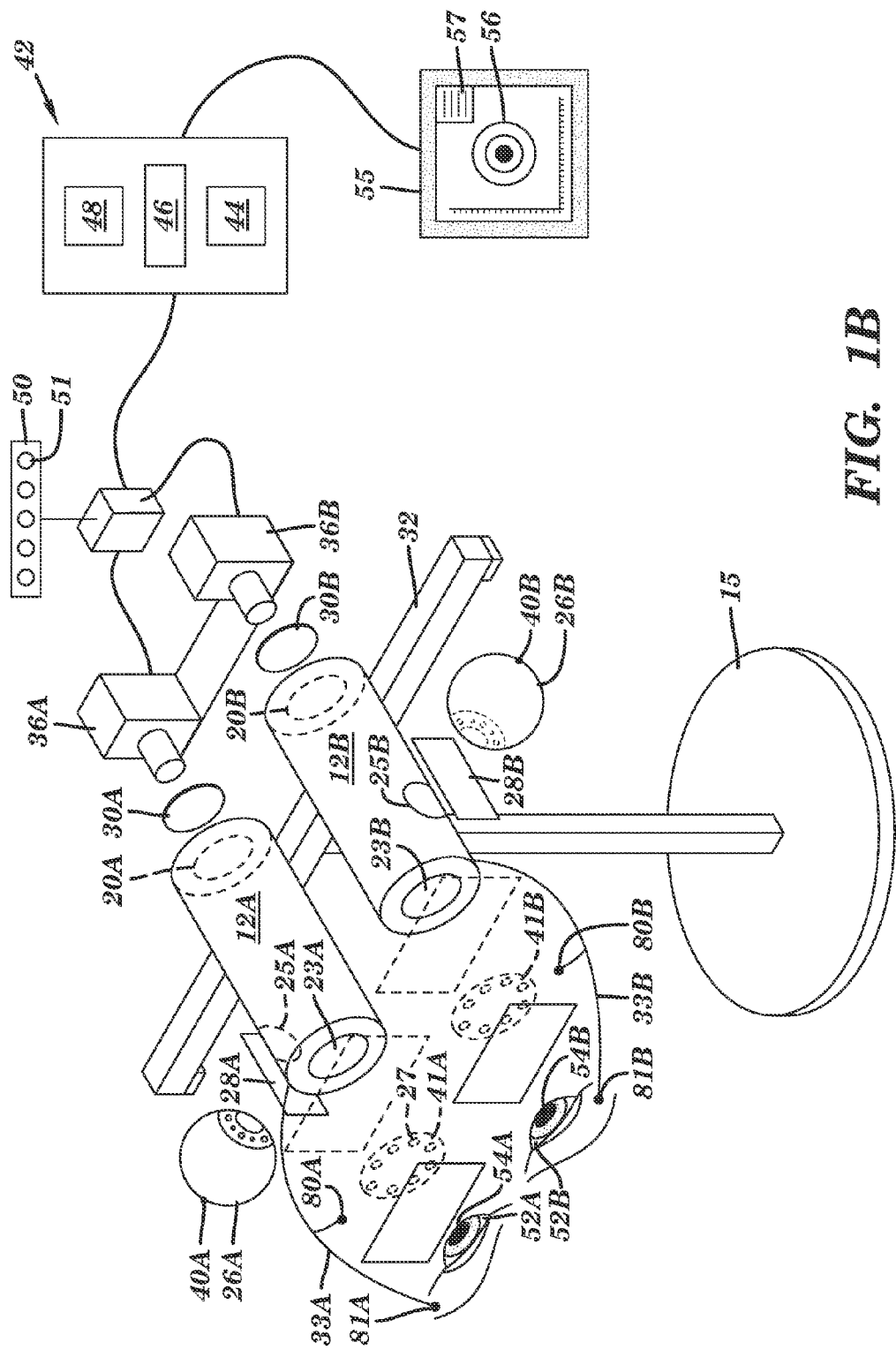
FIG. 1B is perspective view of a system that includes the device shown in FIG. 1A according to another aspect of the invention.

Turning to the drawings, FIG. 1A shows a device 10 for exposing an eye 52A-B to a series of flashes and FIG. 1B shows device 10 when implemented as part of a system for detecting an ocular disorder. In FIG. 1A, device 10 is shown including a pair of eye scopes 12A-B. Each eye scope 12A-B is shown including an ocular aperture 23A-B, a monitoring aperture 20A-B, and a light aperture 25A-B. Further, mirrors 18A-B, and achromatic lenses 16A-B are shown disposed within eye scopes 12A-B, and light sources 26A-B are shown positioned proximate to light apertures 25A-B in eye scopes 12A-B. To test a patient's eyes 52A-B, the patient places both eyes 52A-B so that light passing out of eye scopes 12A-B through ocular apertures 23A-B will enter the eyes 52A-B. Subsequently, one of light sources 26A-B generates a series of flashes (i.e., multiple brief instances of light) that pass through the corresponding light aperture 25A-B, are reflected by the corresponding mirror 18A-B, and pass through the corresponding ocular aperture 23A-B along path 34A-B in the direction shown. As each flash passes through the ocular aperture 23A-B, the corresponding pupil 54A-B of the eye 52A-B responds by adjusting to a certain size/position.

To assist in correctly placing eyes 52A-B for testing, eye scopes 12A-B are shown mounted on an interocular distance adjuster 32. Interocular distance adjuster 32 can be used to adjust the distance between eye scopes 12A-B to correspond with the distance between a particular patient's eyes 52A-B. Further, FIG. 1B shows interocular distance adjuster 32 mounted to a support mechanism 15. In addition to providing stability to eye scopes 12A-B, support mechanism can provide upward and downward adjustments of eye scopes 12A-B. FIG. 1B also shows device 10 including head holder frames 33A-B that include sensor switches 80A-B, 81A-B. Head holder frames 33A-B can assist in holding a patient's head in its desired position during testing, while sensor switches 80A-B, 81A-B can generate a signal (e.g., illuminate a light) when the patient's head is in the desired position for testing. The location of sensor switches 80A-B, 81A-B can be adjusted to conform to various head sizes.

Figure 2:
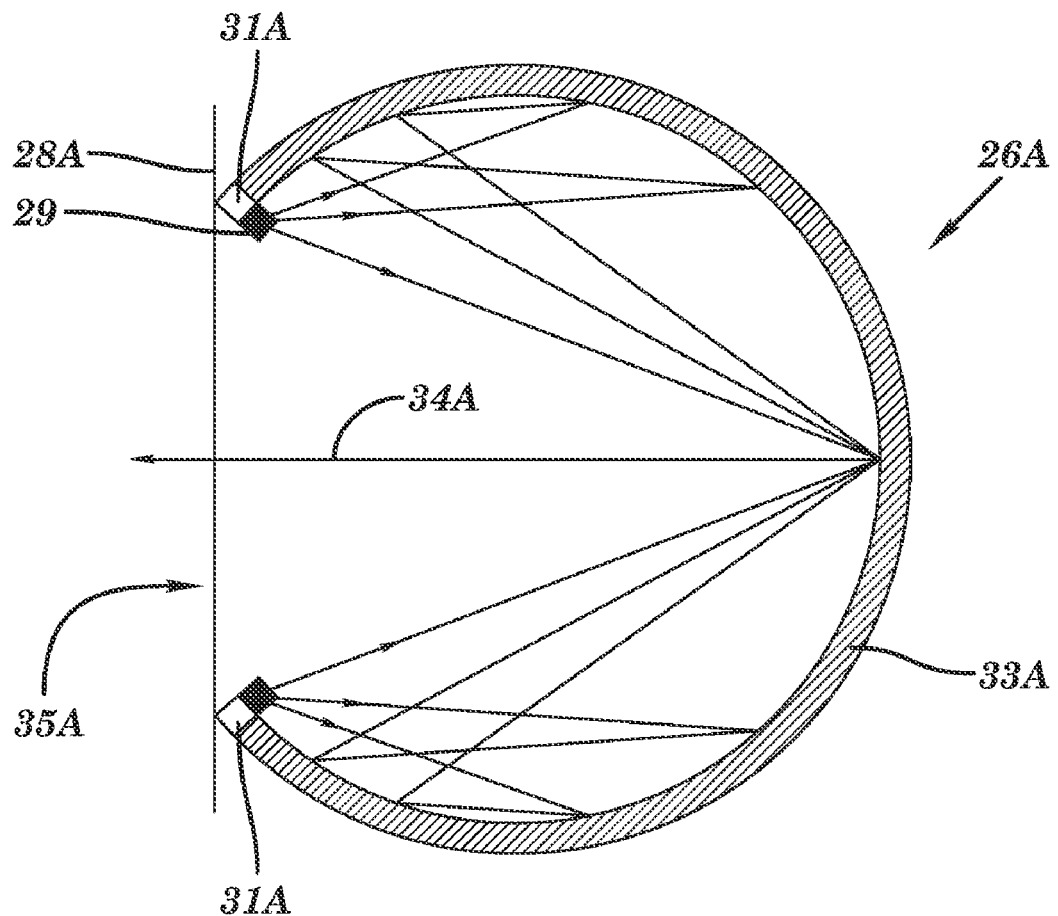
FIG. 2 is a cross-sectional view of a light emitting sphere according to still another aspect of the invention.

As discussed, an eye 52A-B is exposed to a series of flashes generated by one of light sources 26A-B during testing. It is understood that device 10 could include a single light source 26A that generates the series of lights for both eye scopes 12A-B. For example, light source 26A could be moved between eye scopes 12A-B, a system of movable mirrors could be implemented, etc. In one embodiment, each light source 26A-B comprises a light emitting sphere. FIG. 2 shows a preferred embodiment for light emitting sphere 26A adjacent eye scope 12A (FIG. 1A). It is understood that light emitting sphere 26B adjacent eye scope 12B is similar and, accordingly, has like elements. As shown, light emitting sphere 26A comprises an outer portion 31A, a reflective well portion 33A, and an exit port 35A. Disposed along outer portion 31A are a plurality of light sources 29 and, optionally, infrared light sources (e.g., light emitting diodes (LEDs)). In one embodiment, light sources 29 positioned about the outer portion 31A, comprise at least four different, non-spectrally-adjacent hues. For example, light sources 29 can include light sources 29 that generate hues and corresponding peak emission wavelengths that correspond to blue (approximately 430 nanometers), green (approximately 560 nanometers), yellow (approximately 585 nanometers), and red (approximately 660 nanometers). It is understood, however, that other differing peak emission wavelengths, can be incorporated. Further, light sources 29 can generate hues and corresponding peak emission wavelengths that, when combined, correspond to substantially "white" light. Still further, each light source 29 can generate "white" light. The term "white" light can refer to light comprising a combination of two or more wavelengths, which when combined, appear to be white.

As further shown in FIG. 2, light sources 29 point inward toward reflective body portion 33A. As a result, the light emitted from each light source 29 shines into sphere 26A, reflects throughout reflective well portion 33A and eventually reflects back through exit port 35A as a single beam of light 34A in aperture mode. As beam of light 34A passes through exit port 35A, it can pass through a polarizing screen 28A. Polarizing screen 28A can be used to reduce any light artifact when testing a patient under the bright conditions. It is understood that the light will be reflected throughout the entire reflective well portion 33A. The limited number of reflections shown in FIG. 2 is for clarity of illustration.

The use of reflected light presented in aperture mode instead of direct light provides uniformly intense illumination of a limited region of the patient's visual field. Moreover, the use of reflected light is advantageous because no single light source 29, when flashed, can be intense enough to generate a pupillary reflex by pupil 54A-B by itself. Therefore, in order to produce enough stimulus intensity to drive the pupil's reflexes, several LED sources 29 can be "combined" (integrated) by light emitting sphere 26A-B to form beam of light 34A on which the patient's eyes 52A-B should be fixated.

Referring back to FIGS. 1A and 1B, light sources 26A-B can also each include a fixation point 40A-B to which the patient can direct his/her gaze as is known in the art. Fixation points 40A-B provide a central point on which patients should focus while looking into eye scopes 12A-B through ocular apertures 23A-B. When focused on a central point, the testing procedures, described in more detail below, are more accurately performed because the patient's eyes 52A-B do not wander. Each fixation point 40A-B can be provided by two single light sources, via beam splitters, etc. Such fixation arrangements are well known in the art.

The pupillary reflexes of both eyes 52A-B are measured while one eye 52A-B is being exposed to the series of flashes. To assist in measuring the pupillary reflexes of eyes 52A-B, device 10 is also shown in FIG. 1A as including a pair of light sources 41A-B and a pair of achromatic lenses 16A-B. Light from light sources 41A-B reflects off of eyes 52A-B and passes through ocular apertures 23A-B within eye scopes 12A-B along view paths 38A-B in the direction shown. In one embodiment, light sources 41A-B comprise infrared light sources and mirrors 18A-B comprise cold mirrors. The use of infrared light and cold mirrors allows the visible light generated by light sources 26A-B to be deflected by mirrors 18A-B while the infrared light passes through mirrors 18A-B and is allowed to continue towards monitoring apertures 20A-B. Achromatic lenses 16A-B can be used to focus the resulting images of eyes 52A-B for improved measurements of the pupillary reflexes. Still further, infrared light filters 30A-B can also be positioned between a measuring instrument and the patient's eyes 52A-B to ensure that only infrared light reaches the measuring instrument. In this case, infrared light filters 30A-B filter out any non-infrared light that may have passed through cold mirrors 18A-B. It is understood that infrared filters 30A-B could alternatively be provided as a single filter and can be located anywhere between patient's eyes 52A-B and the measuring instrument.

As shown in FIG. 1B, infrared light sources 41A-B can comprise a plurality of infrared lights 27 positioned around eyes 52A-B. For example, infrared light sources 41-B could be provided as a ring of infrared lights 27 positioned about the periphery of ocular apertures 23A-B of each eye scope 12A-B. In one embodiment, infrared lights 27 comprise light emitting diodes (LEDs). In addition, infrared lights 27 can be scuffed or the like so that the light generated by each infrared light 27 is dispersed about a greater surface area of the patient's pupil and as near axial as possible.

During testing, as the test eye 52A-B is exposed to the series of flashes, light sources 41A-B emit infrared light to both eyes 52A-B. The infrared light reflects off eyes 52A-B, passes through eye scopes 12A-B, and through monitoring apertures 20A-B, thereby allowing images of eyes 52A-B to be captured by recording mechanisms 36A-B. In one embodiment, recording mechanisms 36A-B comprise charged coupled devices with significant infrared sensitivity corresponding to the emission of infrared lights 27. However, other known recording means can be used. Further, recording mechanisms 36A-B can provide optical magnification of the images for improved analysis. In any case, recording mechanisms 36A-B record the pupillary reflexes of both eyes 52A-B simultaneously, and can output the recordings to computer system 42 via I/O mechanism 48. The recordings can be converted into recording data by software product 44. Software product 44 can be any number of products known in the art. Computer system 42 can process the recording data to generate an image 56 of one or both eyes 52A-B on video display 55. Further, computer system 42 and/or recording mechanisms 36A-B can determine if the detected pupillary reflexes meet required criteria. For example, only recorded pupillary reflexes that have required criteria comprising: a) measured culmination times of about 0.5 seconds, b) finite latencies, and c) no eye blinks during the recording interval can be accepted. The recording duration for the direct and consensual reflexes can be user-defined, however a duration of approximately one and a half seconds can be used as a default recording interval. If one or both of the pupillary reflexes do not meet all of the required criteria, the eye can be re-exposed to the flash after a suitable interval (e.g., ten seconds).

In one embodiment, analog video cameras 36A-B (e.g., B&W NTSC, also known as RS170) or digital video cameras 36A-B, such as Cameralink® CCD are used, and the images are captured (sampled and quantized) to computer system 42 using a Frame Grabber device 48. The frame grabber 48 can be an external device connected to computer system 42 by USB, Firewire (1394) or the like, or an internal device connected by ISA, PCI, PCI-X, PCI-Express or the like, or a laptop card using PCMCIA (Cardbus) or Express-Card (34 mm or 54 mm) or the like. Further, cameras 36A-B can contain embedded digital signal processors (DSPs) and image processing software that allow for capturing results of pupil measurement and image segmentation and sending of those results to computer system 42. In an alternative embodiment, cameras 36A-B that natively support USB, Firewire, or Ethernet (usually gigabit Ethernet, abbreviated "GigE") can be directly connected to the computer system 42.

The recording data can also be processed to generate image data/graphs 57 for display on video display 55. For example, the dimensions of one or both pupils 54A-B can be displayed in a graph as a function of time. In one embodiment, software product 44 identifies the pupil component of the image and counts the number of pixels in the pupil component of the image to determine the dimensions (e.g., diameter) of pupils 54A-B. Alternatively, software product 44 can implement a scanning line technique with infrared light, as disclosed in U.S. Pat. No. 3,533,683 to Stark et al., hereby incorporated by reference. In any event, once the dimensions of pupils 54A-B are determined, the presence of an ocular dysfunction in one or both of eyes 52A-B can be determined.

Figure 5:
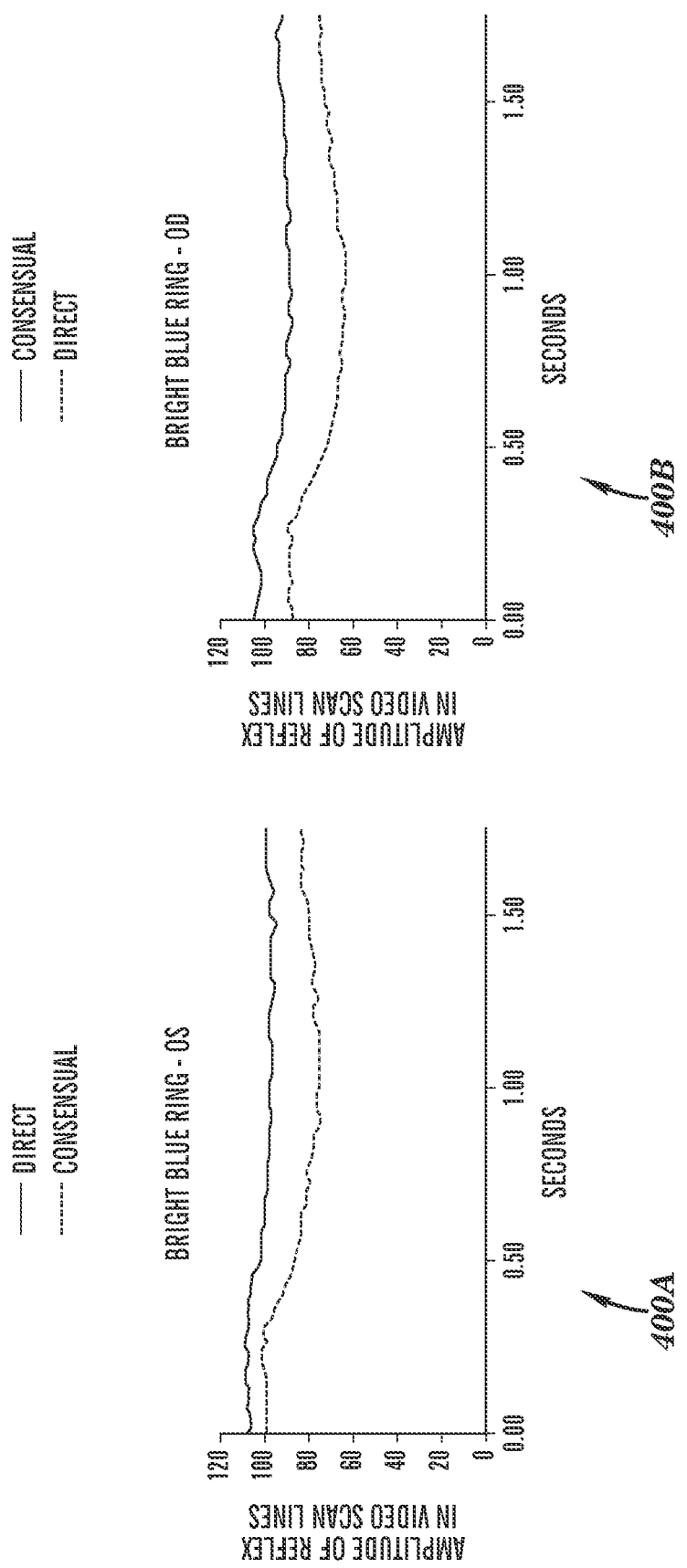
FIG. 5A shows a recording of direct and consensual pupillary reflexes evoked by a flash exposed to the left eye of a patient according to one aspect of the invention.
FIG. 5B shows a recording of direct and consensual pupillary reflexes evoked by a flash exposed to the right eye of a patient according to another aspect of the invention.

FIGS. 5A and 5B show illustrative graphs 400A-B generated from the recording data that can be displayed on video display 55 for analysis by an operator. Graph 400A represents recording data when a left eye was exposed to the flash, and graph 400B represents recording data when a right eye was exposed to the same flash. In both cases, the flash comprised a bright blue beam of light. In each graph 400A-B, the video frames that were recorded in a time interval of 1.75 seconds following the onset of a flash were analyzed to generate the data shown. In this case, the pupil size is shown as a number of video scan lines obtained from each video frame. In each graph 400A-B, data for both the exposed eye (direct) as well as the other eye (consensual) are charted. Graphs 400A-B allow an operator to visually analyze the pupillary reflexes of both eyes to the exposed flash.

Returning to FIG. 1B, the system further includes a control panel 50 having one or more control adjusters 51. Control adjusters 51 allow an operator to adjust the video features (e.g., height and width) of an image as it appears on the video display 55 and to define a region of interest in the video image. In particular, an operator can adjust the vertical and/or horizontal dimensions of a window of interest of the video display 55 and the location with reference to the corneal region of the eye to be captured by the recording mechanisms 36A-B.

Electronic overlay board 46 can also be included in computer system 42 for producing an electronic overlay. The electronic overlay can be used to further limit the fields of view of recording mechanisms 36A-B. The overlay feature can be enabled by overlay board 46 in computer system 42 and can be implemented using technology known in the art. The electronic overlay can also be positioned by one or more control adjusters 51. Control adjusters 51 can allow a user to customize the field of view for a particular patient as the user views images 56 of eyes 52A-B on video display 55. Specifically, once a patient is properly positioned so pupils 54A-B are in the field of view, an operator can view video display 55 and adjust (position and size) the overlay 60 until it only overlays pupils 54A-B of the patient. Once the overlay is in its proper position, and the threshold is set, the image is ready for processing. In one embodiment, overlay area 60 is circular and can be sized to fit within the pupil. A narrower overlay can be used as long as it covers, i.e. can measure, the pupil diameter.

Figure 3:
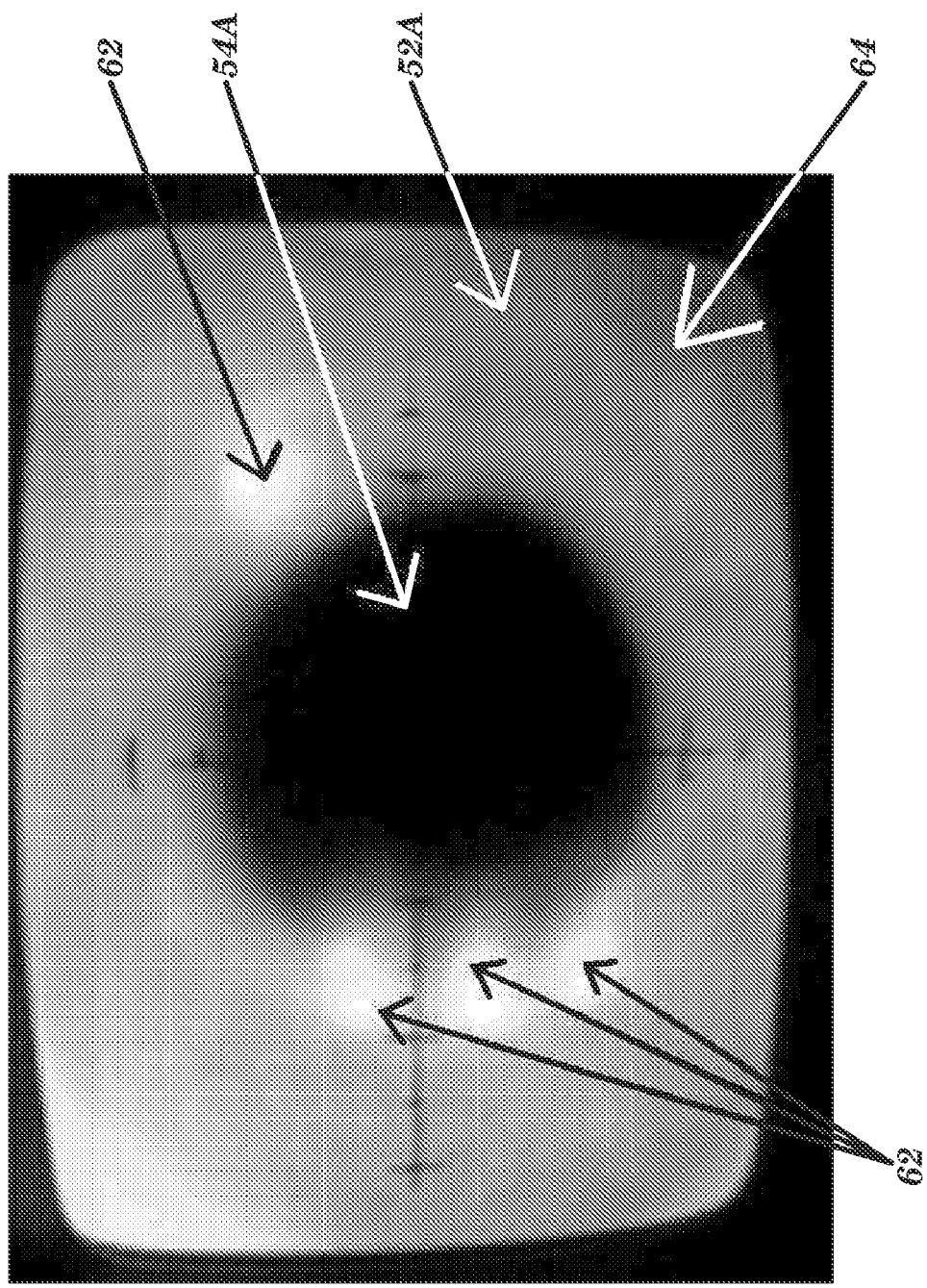
FIG. 3 shows a recorded image of an eye according to yet another aspect of the invention.
Figure 4:
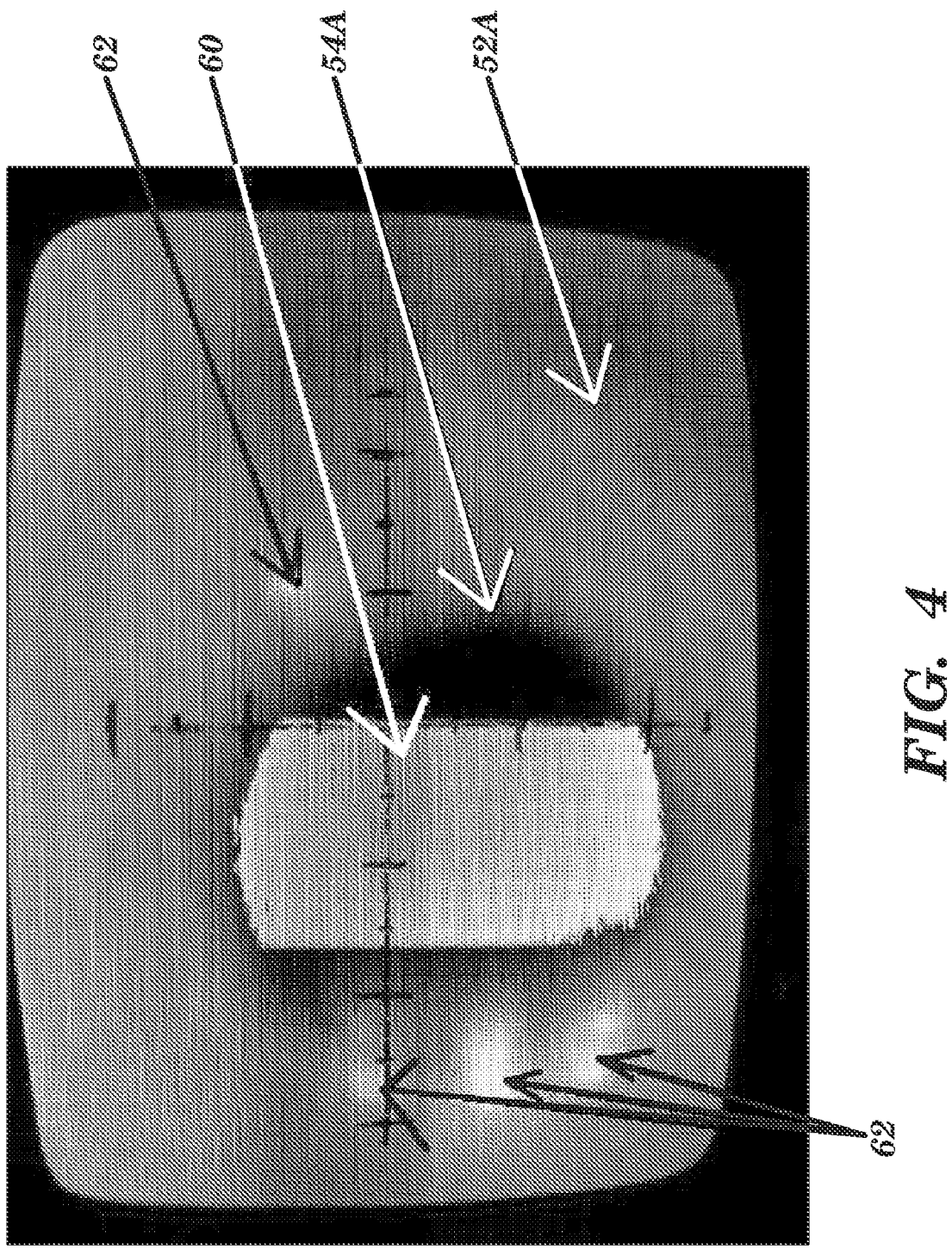
FIG. 4 shows a recorded image of an eye that includes an overlay feature according to another aspect of the invention.

For example, FIG. 3 shows an image of eye 52A without the overlay features. As shown, the field of view 64 extends beyond the pupillary boundary (the periphery of the pupil 54A) and includes noise 62. For example, noise 62 can comprise a series of bright points that can be generated when infrared lights 27 (FIG. 1B) are used to illuminate eye 52A. In any event, noise 62 can interfere with the accurate analysis of the eye image and its corresponding dimensional data. As shown in FIG. 4, the use of an electronic overlay limits the field of view of recording mechanism 36A (FIG. 1A) to an overlay area 60 that is defined primarily by pupil 54A, thereby excluding noise 62 and/or any other extraneous features.

Figure 6:
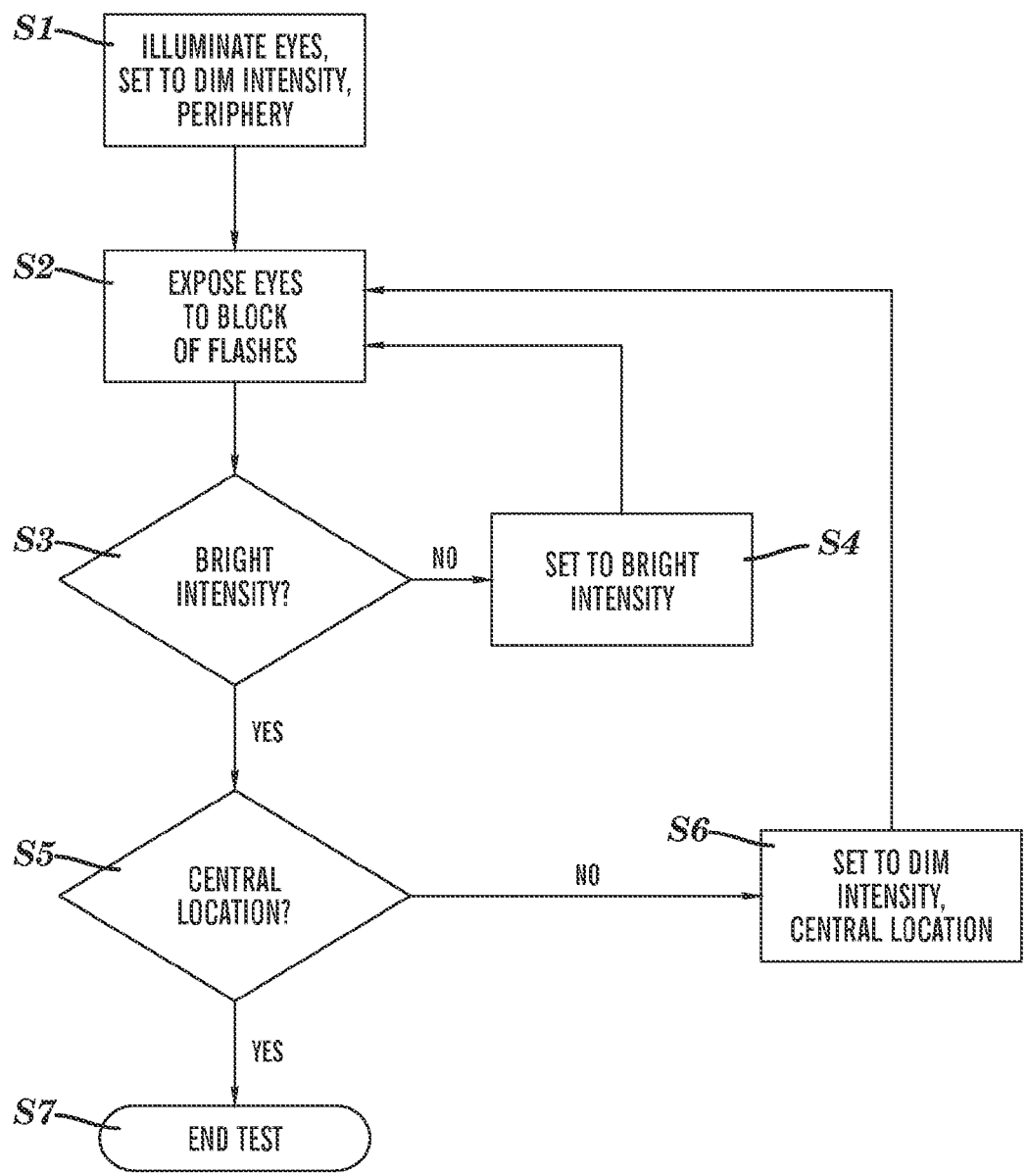
FIG. 6 shows illustrative method steps according to one aspect of the invention.

FIG. 6 shows illustrative method steps for testing eyes 52A-B (FIG. 1A) according to one embodiment of the invention. In the embodiment shown, eyes 52A-B are exposed to a "block" of flashes in step S2. A block of flashes comprises a series of flashes to which each eye 52A-B of the patient is exposed. In one embodiment, a first eye can be exposed to the series of flashes, followed by the second eye being exposed to the same series of flashes. Each flash in the series of flashes varies from the other flashes in the series by at least one of: location in the visual field, luminosity, and/or chromatically. In the embodiment shown, each flash in the series of flashes to which each eye is exposed in step S2 varies chromatically from the other flashes in the series. For example, the series of flashes can comprise four flashes, in which the first flash is red, followed in order by green, blue, and yellow flashes. Further, the series of flashes is repeated for each combination of two settings for luminosity (i.e., dim and bright), and two locations for the field of view (i.e., periphery and central). It is understood, however, that numerous variations are possible.

Figure 7:
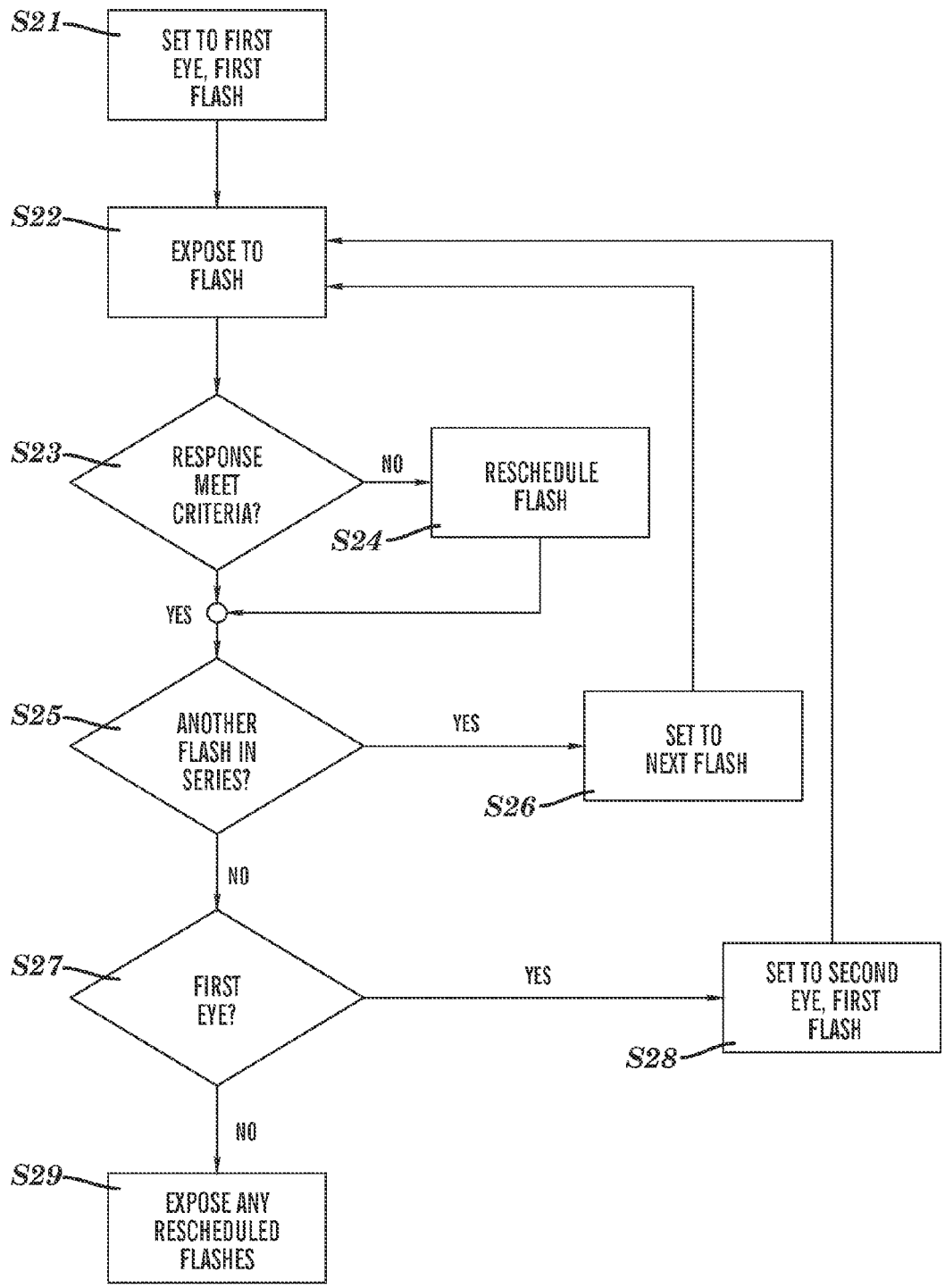
FIG. 7 shows illustrative method steps according to another aspect of the invention.

In any event, once a patient is properly positioned proximate device 10 (FIG. 1A) for testing, eyes 52A-B can be illuminated using light sources 41A-B (FIG. 1A) in step S1, and the settings for a first block of flashes are set so that each flash has a dim intensity, and a location in a periphery of the visual field. In step S2, the eyes are exposed to the block of flashes. FIG. 7 shows illustrative steps used to expose the eyes to the block of flashes. In this case, each flash in the series of flashes varies chromatically from the other flashes in the same series of flashes. In step S21, device 10 (FIG. 1A) is set to expose a first eye to the first flash in the series of flashes. In step S22, the eye is exposed to the flash. In step S23, it is determined if the pupillary reflexes that were detected by, for example, recording mechanisms 36A-B (FIG. 1A) include the required criteria (e.g., eyes did not blink). If the pupillary reflexes do not meet the required criteria, the flash is rescheduled in step S24 to be re-exposed at the end of the block. In step S25, it is determined if there are any additional flashes in the series. If additional flashes remain, device 10 is set to expose the next flash in step S26, and flow returns to step S22 where the flash is exposed. Once all flashes in the series have been exposed, it is determined in step S27 if both eyes have been exposed to the series. If only the first eye has been exposed, flow continues to step S28 in which device 10 is set to expose the second eye to the first flash in the series, and flow returns to step S22 where the flash is exposed. Once the series of flashes has been exposed to both eyes, flow continues to step S29 wherein any rescheduled flashes are re-exposed in a similar manner. To re-expose each rescheduled flash, the eye and the corresponding flash in the sequence are stored and device 10 is set appropriately between each flash. It is understood that the method steps are only illustrative, and various alternatives are possible. For example, a flash can be rescheduled to occur at the end of the series of flashes, or the flash could be re-exposed as the next flash.

Returning to the embodiment shown in FIG. 6, once the eyes have been exposed to the block of flashes in step S2, it is determined what intensity was used in step S3. If the dim setting for luminosity was used, then the luminosity is set to the bright setting in step S4, and flow returns to step S2 wherein the eyes are exposed to the block of flashes using the new luminosity setting. If the bright luminosity setting was used, the location setting that was used for the block of flashes is determined in step S5. If the periphery location was used, then the location setting is changed to the central location in step S6. Additionally, the luminosity setting is changed back to dim so that both the dim and bright settings will be used for the new location. Once the eyes have been exposed to the block of flashes having bright intensity and located in the central location of the field of view, the test is ended in step S7.

In one embodiment, each series of flashes comprises four flashes (e.g., red, green, blue, yellow). Consequently, each block of flashes would comprise eight flashes. Further, each flash in each series of flashes can be spaced from a previous flash by approximately ten seconds. When repeated for each combination of two luminosity settings, and two different locations in the field of view, each block of flashes would be performed four times. As a result, the entire test (i.e., thirty-two flashes) can be run in approximately five minutes (without any rescheduled flashes).

As previously noted, the recorded pupillary reflexes can be processed to detect the presence of an ocular dysfunction. For example, the pupil sizes can be used to determine the Relative Afferent Pupillary Defects (RAPD) evoked by each flash. By exposing both eyes to the same series of flashes, and simultaneously measuring the direct and consensual pupillary reflexes for each flash, two values for the RAPD can be calculated. First, when the left eye was exposed to the series of flashes, the RAPD for each flash can be calculated by subtracting the direct pupillary reflex of the left eye (OSD) from the consensual pupillary reflex of the right eye (ODC), or ODC-OSD. Second, the RAPD can be calculated when the right eye was exposed to the same series of flashes. In this case, the RAPD for each flash can be calculated by subtracting the consensual pupillary reflex of the left eye (OSC) from the direct pupillary reflex of the right eye (ODD), or ODD-OSC. A non-zero result for either of the calculations indicates that an ocular dysfunction is present. The size of the difference provides some indication of the extent of the dysfunction. Further, the sign of the difference indicates the eye in which the defect is present. For example, since the left eye was subtracted from the right eye for each flash in the table below, a positive value indicates a left afferent defect (LA) and a negative value indicates a right afferent defect (RA).

| RAPD Magnitudes and Their Classification as Left or Right Afferent Defects as Determined from Reflex Amplitudes | | | | |
|---|---|---|---|---|
| S-POAG | Red | Yellow | Green | Blue |
| Bright Disk | | | | |
| ODC-OSD defect | 0.45 (LA) | 0.30 (LA) | 0.30 (LA) | 1.15 (LA) |
| ODD-OSC defect | 1.45 (LA) | −0.25 (RA) | −1.25 (RA) | 1.35 (LA) |
| Bright Ring | | | | |
| ODC-OSD defect | 0.95 (LA) | −2.00 (RA) | 2.80 (LA) | 4.65 (LA) |
| ODD-OSC defect | 2.65 (LA) | −3.30 (RA) | 1.25 (LA) | 1.30 (LA) |
| Dim Disk | | | | |
| ODC-OSD defect | −0.95 (RA) | 0.55 (LA) | 0.40 (LA) | −2.10 (RA) |
| ODD-OSC defect | 0.00 | 0.25 (LA) | 2.30 (LA) | −1.20 (RA) |
| Dim Ring | | | | |
| ODC-OSD defect | 2.85 (LA) | 0.20 (LA) | 1.90 (LA) | 0.65 (LA) |
| ODD-OSC defect | 5.65 (LA) | −0.15 (RA) | 2.10 (LA) | 5.30 (LA) |

A multivariate mode of analyses can also be used to further discriminate between the various optic dysfunctions of, for example, patients diagnosed with the glaucoma group of diseases. For example, the Pearson product moment correlation coefficients between the matrices of the RAPDs of any number of selected patients' eyes can be calculated so as to determine the extent of the resemblance between the pattern of RAPDs of each of these patients' individual eye or eyes. In order to obtain the best results, the flashes can be provided in the same, or as close to the same as possible, sequence to each patient. A high correlation between the ocular dysfunctions of a first patient and a second patient known to have a particular ocular disorder can indicate that the first patient also has the ocular disorder. When data from numerous patients is used for each disorder, a set of inter-correlation matrices can be constructed as shown in FIG. 8. The inter-correlation matrices can provide the ability to compare relevant correlations between a test patient's data and that of index patients having various diagnosed ocular disorders. The inter-correlation matrices allow precise quantitative assessment of the resemblance of the data recorded for a test patient to the data recorded for patients clinically diagnosed as having various ocular dysfunctions.

The system and method described herein have been shown to screen for glaucomatous patients. Recordings were obtained from five groups of eight diagnosed subjects, each classified as either advanced (GA) or early (GE) glaucoma, or suspects (GS), with groups of normal (N) exams and retinal (R) pathologies (also n=8 each) serving as controls. Advanced and early glaucoma patients (subjects) were identified by an ophthalmologist using the patient's perimetric exam results. Stages of glaucoma were rated on a 10-point scale, with zero identifying suspects and 9 representing the most advanced glaucoma. The eight patients with ratings of equal to or greater than "5" were deemed to represent advanced glaucoma. Eight patients diagnosed by their clinician as glaucoma suspects, had no indication of field defects and were rated zero. These eight comprised the glaucoma suspect group. Table 1 below is a confusion matrix showing classifications of patients by designated clinical group following Discriminant Analyses.

TABLE 1

| Confusion Matrix for the 40 patients | | | | | | | |
|---|---|---|---|---|---|---|---|
| Prior | Predicted Classification | | | | | | Success |
| Classification | GA | GE | GS | N | R | Sum | Rate* |
| GA** | 3 | 1 | 2 | 2 | 0 | 8 | 0.375 |
| GE** | 0 | 6 | 1 | 1 | 0 | 8 | 0.75 |
| GS** | 0 | 2 | 4 | 0 | 2 | 8 | 0.50 |
| N** | 4 | 1 | 1 | 1 | 1 | 8 | 0.125 |
| R** | 0 | 0 | 0 | 1 | 7 | 8 | 0.875 |
| Sum | 7 | 11 | 8 | 5 | 10 | 40 | 0.525 = Mean |

*a priori probability = 0.20
**GA = Advanced glaucoma, GE = Early glaucoma, GS = Suspect glaucoma, N = Normal exam, R = Retinal Pathology Combining the three glaucoma groups (suspect, early and advanced) and the two non-glaucoma groups (normal and retinal) produced a 2×2 Contingency Table (Table 2, below). Expected frequencies shown in Table 2 are large enough to allow for assessment of overall probabilities of success and failure, using a Chi square test without correction. This consolidation yielded a Chi square value of 7.1 (p<0.01)(df=1) and shows the test can successfully screen for glaucomatous patients in a population including other ocular (retinal) disorders and patients with normal indicators.

TABLE 2

| 2 × 2 Contingency Table for Combined Groups | | |
|---|---|---|
| Test Results | Of GA, GE and GS Patients | Of R and N Patients |
| Number Identified as GA, GE, or GS | 19 (15)* | 5 (9)* |
| Number Identified as R or N Patients | 6 (15)* | 10 (6)* |

( )* = Expected frequency

Additionally, the system and method described herein have been further shown to screen for neurodegenerative diseases. Table 3 below shows a confusion matrix of 64 patients when subjected to a holdout (cross-validation) discriminant analysis. The mean success rate exceeds the a priori probability of 0.25, and so does the success rate of each of the four groups: (g) glaucoma, (n) normal, (r) retinal and (s) glaucoma suspect.

TABLE 3

Confusion Matrix of 64 Patients

| actual | predict | | | | Total | % correct |
|---|---|---|---|---|---|---|
| | g | n | r | s | | |
| g | 15 | 3 | 1 | 3 | 22 | 68.18% |
| n | 5 | 5 | 0 | 5 | 15 | 33.33% |
| r | 2 | 0 | 6 | 2 | 10 | 60.00% |
| s | 8 | 1 | 1 | 7 | 17 | 41.18% |
| Total | 30 | 9 | 8 | 17 | 64 | 51.56% |

Table 4 below shows a confusion matrix of 78 patients when subjected to a holdout (cross-validation) discriminant analysis. The mean success rate exceeds the a priori probability of 0.2, and each of the four groups exceeds this as well (g) glaucoma, (n) normal, (r) retinal, (s) glaucoma suspect, and (ms) multiple sclerosis. This shows the ability of the test not only to distinguish between the previous 4 clinical categories, but the neurodegenerative disorder, MS as well.

TABLE 4

Confusion Matrix of 78 Patients

| actual | predict | | | | | Total | % correct |
|---|---|---|---|---|---|---|---|
| | g | ms | n | r | s | | |
| g | 16 | 0 | 4 | 1 | 1 | 22 | 72.73% |
| ms | 5 | 6 | 1 | 1 | 1 | 14 | 42.86% |
| n | 4 | 1 | 4 | 0 | 6 | 15 | 26.67% |
| r | 0 | 4 | 0 | 2 | 4 | 10 | 20.00% |
| s | 6 | 1 | 4 | 1 | 5 | 17 | 29.41% |
| Total | 31 | 12 | 13 | 5 | 17 | 78 | 42.31% |

Table 5 below shows a confusion matrix that compares MS patients to the normal group only. The success rate exceeds the a priori probability of 0.5 for both categories.

TABLE 5

Confusion Matrix Comparing Multiple Sclerosis (MS) to Normal

| actual | predict | | Sum | Success Rate |
|---|---|---|---|---|
| | n | ms | | |
| n | 13 | 4 | 17 | 0.765 |
| ms | 5 | 9 | 14 | 0.643 |
| | | | Total # | Average Success Rate |
| Sum | 18 | 13 | 31 | 0.71 |

When the MS and N data (above) is subjected to a chi-square analysis, a p-value 0.02 ($X^2$ Value 5.24, 1 df) is shown. These findings suggest that pupillometry detects both optic neuropathy and neurodegenerative diseases. What was found with these 78 patients confirms that MS can be detected with this technology and that glaucoma can be considered a neurodegenerative disease.

Figure 9:
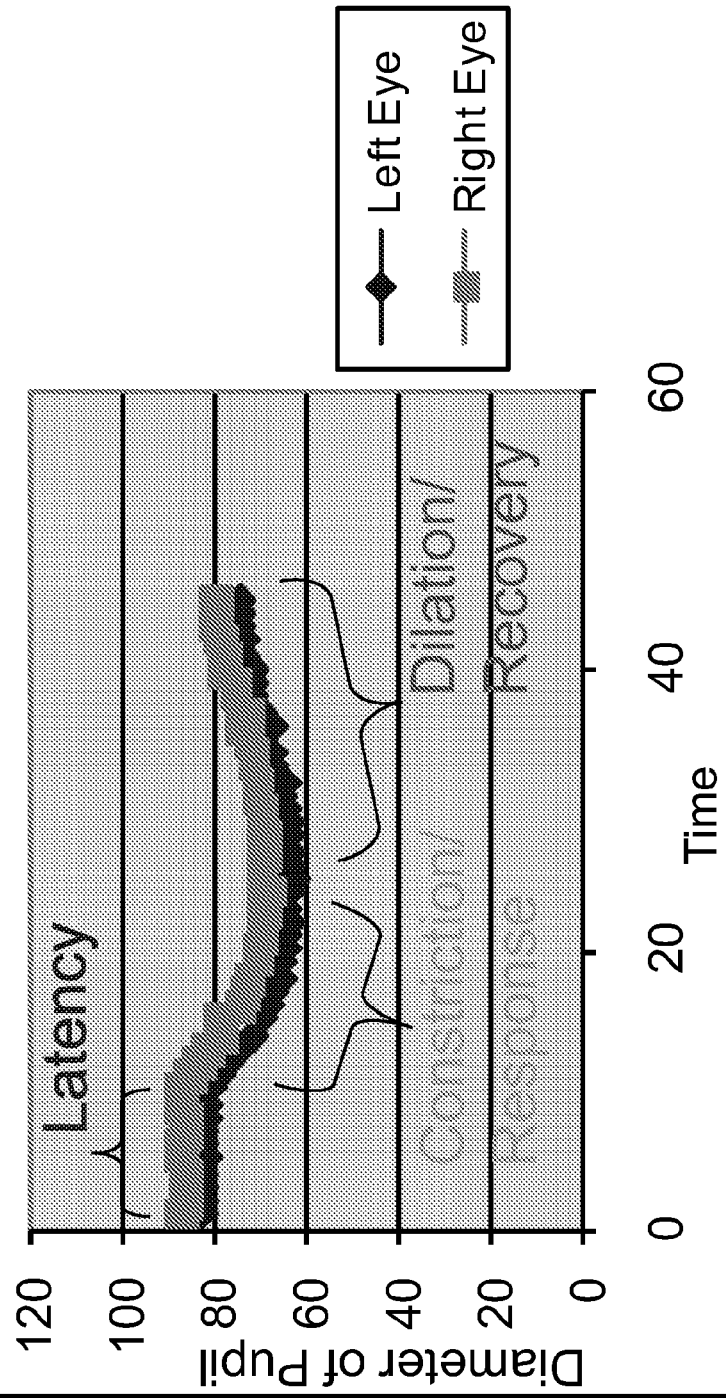
FIG. 9 shows an illustrative graph of pupillary responses to a green light stimulus according to another aspect of the invention.
Figure 10:
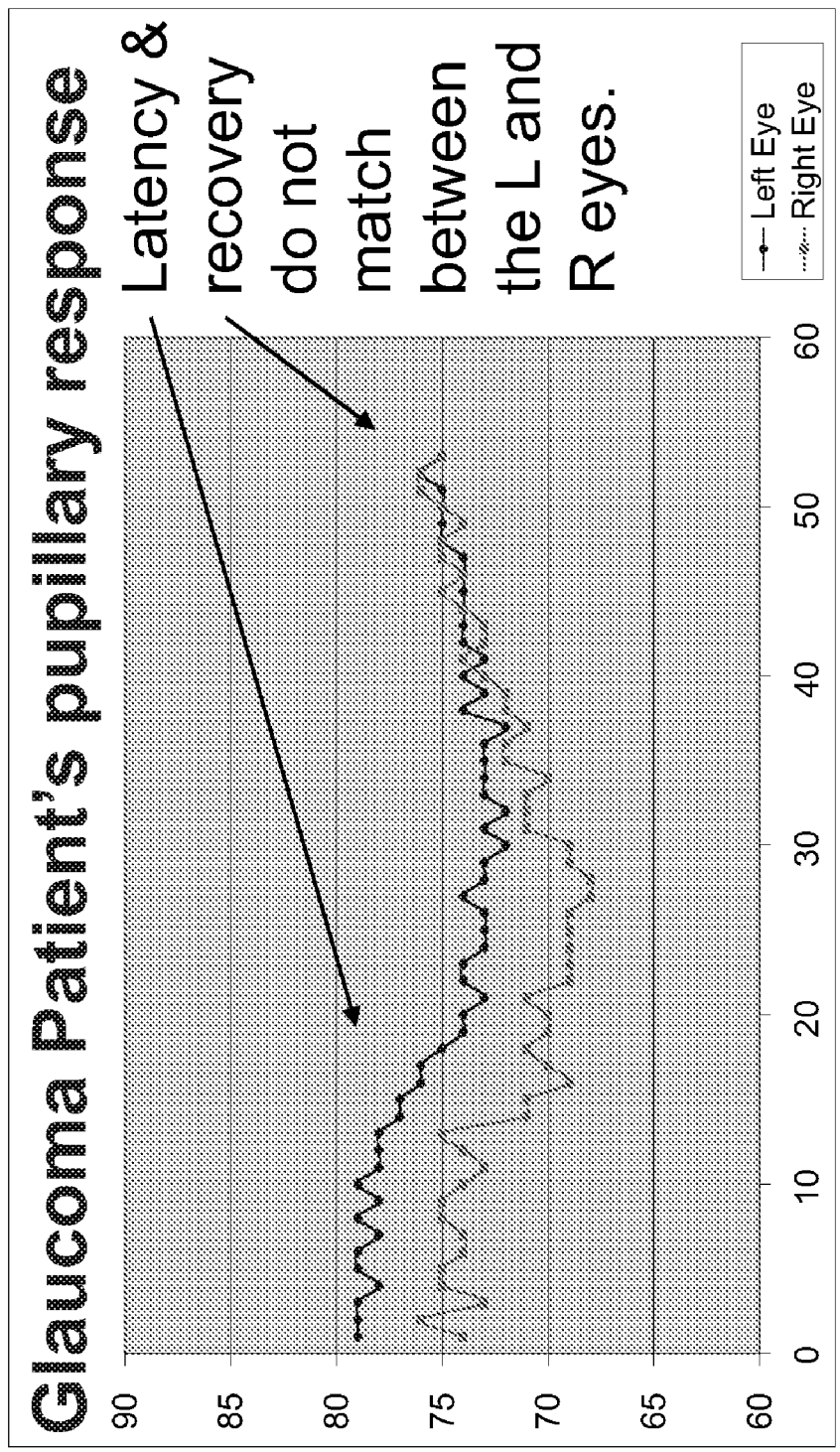
FIG. 10 shows an illustrative graph of a Glaucoma patient's response to a light stimulus according to another aspect of the invention.

FIG. 9 further shows an illustrative graph of pupillary responses to a green light stimulus according to another aspect of the invention. The graph illustrates the latency period, the time it takes the pupils to respond to the flash, the constriction period and the escape, or dilation period. This shows that both left and right eye have the same response to the green flash of light. Additionally, the test can be used to identify patients having other disorders, such as optic neuritis, macular degeneration, and multiple sclerosis.

An embodiment of the invention can identify individuals having a biomarker of a predisposition of a disorder, such as Alzheimer's. In general, a biomarker is defined as a measure of a biological process or other feature that can be correlated with some aspect of normal body function, an underlying disease process, or a response to a treatment. For example, blood pressure can be objectively and easily measured and acts as a biomarker of both normal cardiovascular function, and (when high) of potential cardiovascular disease. There are several types of biomarkers. These include: a disease trait biomarker, which predicts a likelihood that a given individual will get a disease and may be present even in the absence of actual disease (e.g., genetic predisposition); a disease state biomarker, which enables an identification that a given individual has a disease; a disease rate biomarker, which marks progression of a disease over time; and translational biomarkers, which can predict whether an individual will respond to a particular treatment or not, or whether a drug is reaching and acting on its biological target. Based on the analysis to date, an embodiment of the invention can identify a disease trait biomarker and/or a disease state biomarker for Alzheimer's in individuals.

An embodiment of the invention provides a solution that improves the manual Swinging Flashlight Test (SFT) process. For example, am embodiment of the invention can automate the SFT process as well as make the process more useful by enabling one or more of: an automated, standardized, repeatable, implementation of the SFT process; high-speed observations in the Marcus Gunn pupil response and/or slower speed playback, which enables the detection of very subtle differences in the response; highly reproducible test conditions for each session; juxtaposed display of pupils (e.g., opposing halves of each pupil placed side by side in a single image); session recording for later playback, review, and analysis; magnification of pupil images; and/or the like.

Returning to FIGS. 1A-B, an embodiment of device 10 can include light sources 26A-B that generate white light. For example, light sources 26A-B can include a white light source 29 (FIG. 2), such as a white LED, which generates white light, e.g., light having a CIE color temperature of approximately 5500K. However, it is understood that any "white" light can be utilized, such as light having any "white" CIE color temperature, light within the "white" range of the Plankian locus diagram, and/or the like. In an embodiment, each light source 26A-B can include a plurality (e.g., five) of color-specific light sources 29 (e.g., LEDs), each of which emits light of a particular color, the combination of which yields white light. The light emitted by the light sources 29 can be combined using a light emitting sphere 26A (FIG. 2), which can comprise a diameter of, for example, approximately twenty-five millimeters. Further, each light source 26A-B can include LCD or OLED flat panel(s). Regardless, each light source 26A-B can provide sufficient color saturation to emit "white" light.

An embodiment of device 10 can include an automatic shutter to create "disk" and "ring" visual field targets as part of light sources 26A-B. For example, a light source 26A-B for an eye can include shutter that includes an LCD cell arranged between two polarizers. Each LCD cell can be dark until power is applied, which undoes the polarization to allow light to pass through. Device 10 can include a driver circuit that independently controls the two regions using any solution. In this case, the LCD polarizing filter can have two independently controlled regions that are dark or light, and provides electronic and independent control with a fast and repeatable switching time. A very thin wire lead enables light sources 26A-B to make a concentric image.

A stimulation process similar to the SFT process can be implemented by computer system 42. To this extent, software product 44 can enable computer system 42 to perform the stimulation process, which simulates the swinging back and forth, and I/O mechanism 48 can include an I/O board for controlling a white light source 26A-B for each eye. During the stimulation process, a first white light source, such as light source 26A, stimulates one eye for a period of time while the other eye is not stimulated, followed in quick succession by a second white light source, such as light source 26B, stimulating the other eye for a period of time while the first eye is not stimulated. The alternating stimulations can be repeated several times.

While performing the stimulation process, computer system 42 can acquire and use pupil information to determine the RAPD. To this extent, computer system 42 can perform a direct comparison of a set of parameters of the pupil information, such as a constriction amplitude, a constriction latency, a constriction culmination time/velocity, a dilation time/velocity, and/or the like. Furthermore, the operator can make a subjective determination of a positive or negative sign of RAPD based on the displayed images of the pupils (FIGS. 11-13) which can be reviewed under magnification, time expansion (slow motion) or the like. Computer system 42 can classify any differences in the set of parameters between the two eyes using, for example, a normative distribution, compare the differences to a database of results from known pathologies, and/or the like.

Each repetition can be substantially identical, or can approximate a filter method, in which the stimulus for one or both eyes is made dimmer. In the latter case, computer system 42 can adjust the stimulus generated by light sources 26A-B in successive "swings" until one or more of the parameters of the pupil information are equalized. For example, computer system 42 can control light sources 26A-D (e.g., a set of white LEDs) using pulse width modulation (PWM) or the like. After determining when the parameter(s) is/are equalized, computer system 42 can define the RAPD as the difference in light levels of the stimuli that were required to achieve equality. Regardless, computer system 42 can convert an RAPD score to log units, which will enable comparison of the score with traditional methods. Further, computer system 42 can store the results of an stimulation process using a standardized record keeping solution, e.g., a format compatible with the military Electronic Medical Record, or the like.

An embodiment of computer system 42 can enable the display of one or more visual aids on video display 55 to assist a clinician or the like in the detection of asymmetric pupillary reflexes. For example, recording mechanisms 36A-B can capture a series of images (e.g., video) of the pupils and provide the image data to computer system 42. Computer system 42 can process the image data of each pupil to isolate half of the pupil using any solution, e.g., the right half of the right pupil and the left half of the left pupil. Computer system 42 can merge the two halves (one of each pupil) into a single image that is provided for display on video display 55. In this case, the operator will view an image that includes half of each pupil. While performing the stimulation process the operator will be able to readily identify any differences between the contractions/dilations of the eyes.

Computer system 42 can perform image processing in order to identify the center of each pupil. For example, recording mechanisms 36A-B can convert each video frame to a digital image, which can be provided to computer system 42 for processing. This can allow computer system 42 to display the eye images simultaneously and on the same display 55 as the software product 44.

Figure 11:
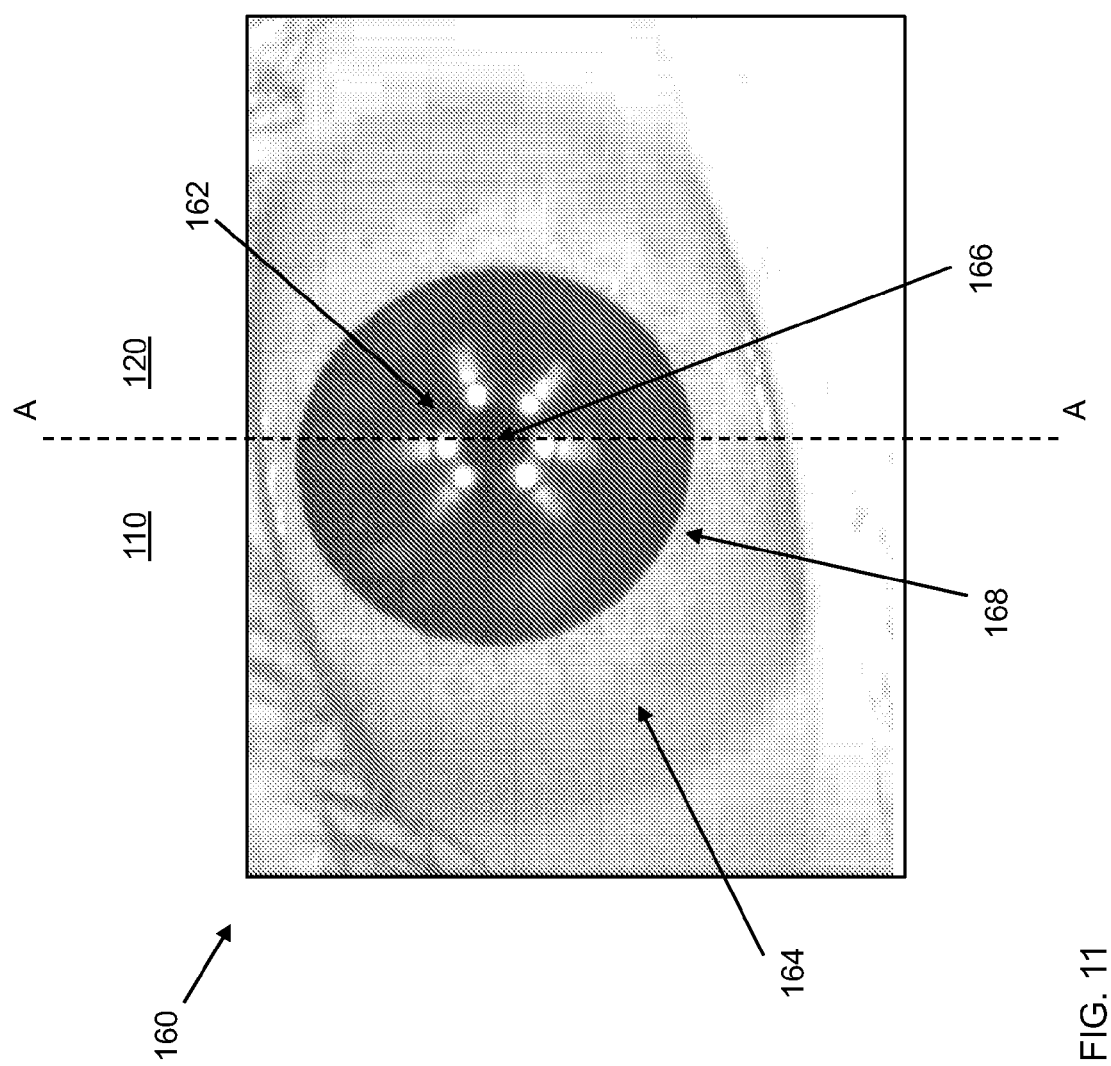
FIG. 11 shows an image of a first eye according to aspects of the invention.
Figure 12:
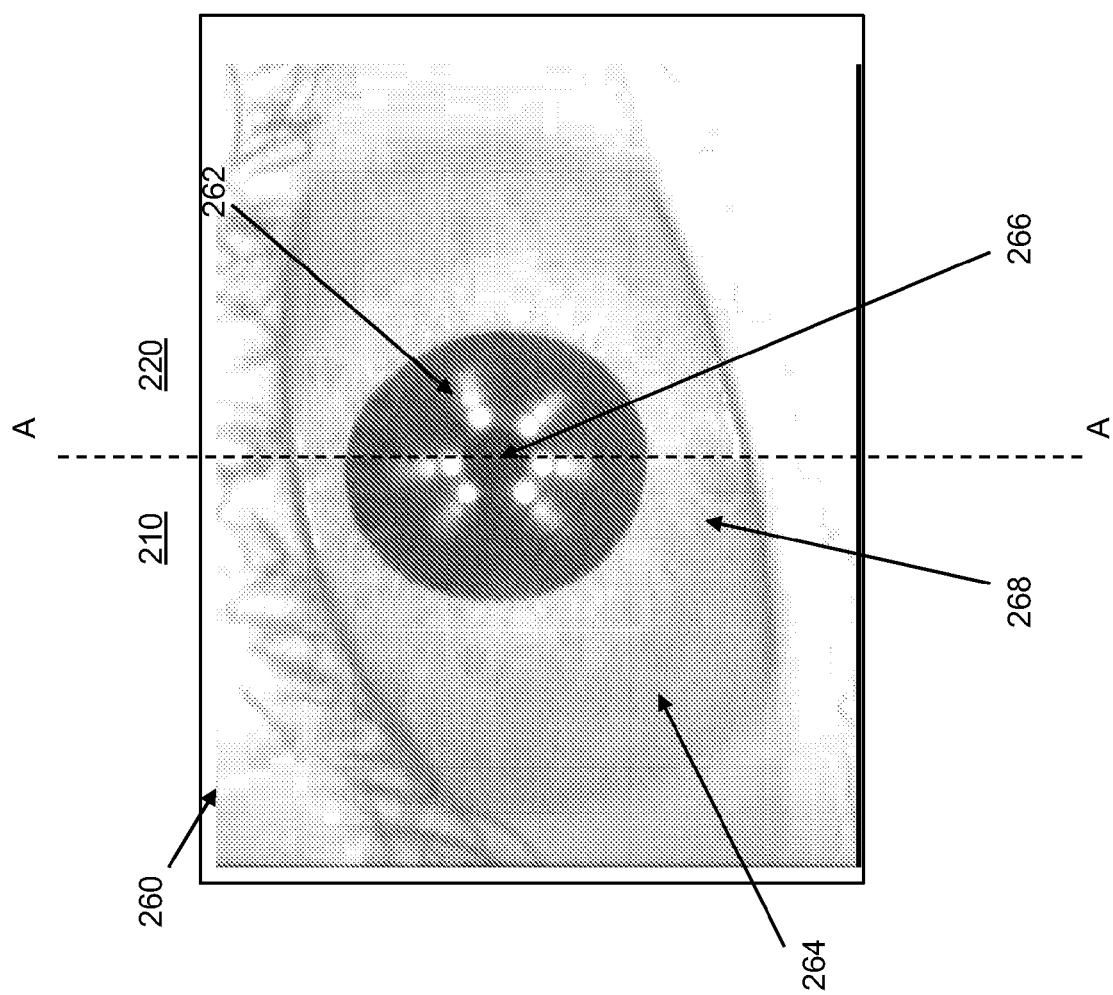
FIG. 12 shows an image of a second eye according to aspects of the invention.
Figure 13:
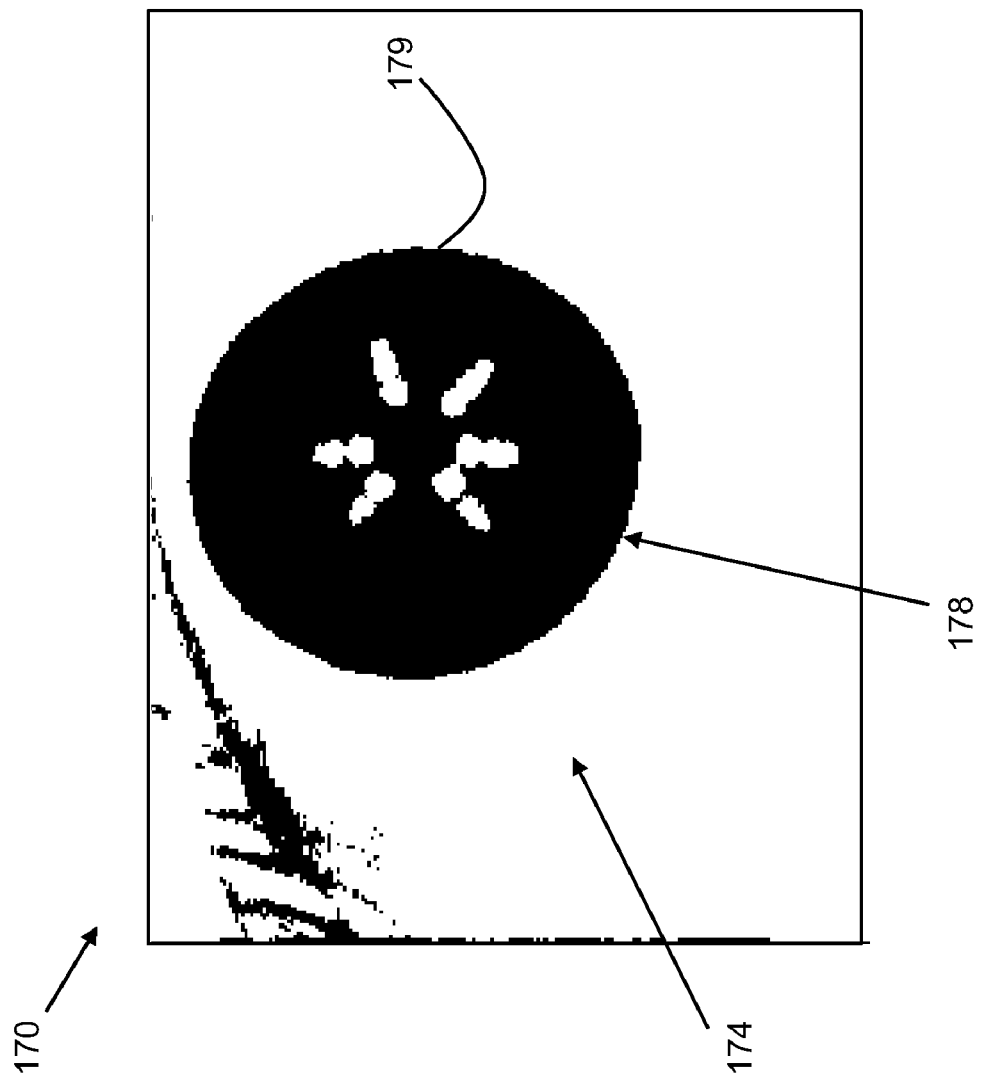
FIG. 13 shows a binarized image of the first eye according to aspects of the invention.
Figure 14:
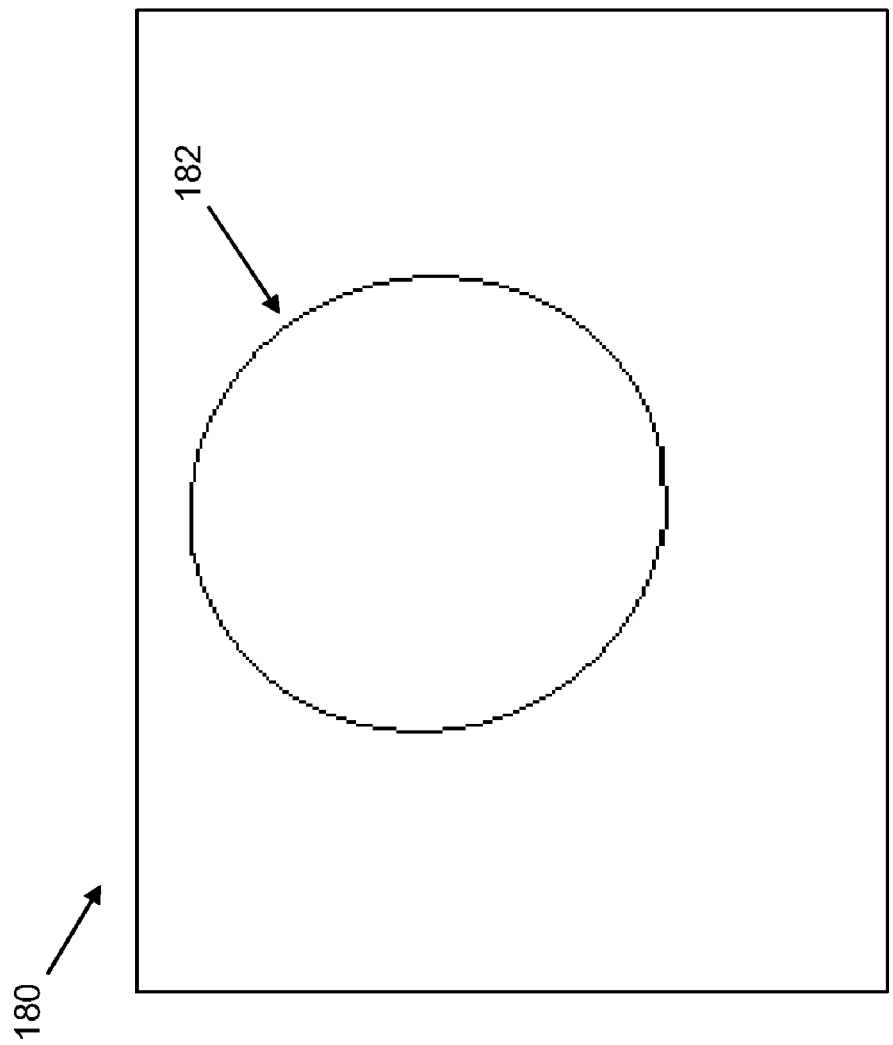
FIG. 14 shows a best-fit ellipse image of the first eye according to aspects of the invention.

Referring to FIGS. 11-14, illustrative images of a first eye and a second eye of a patient are shown. In one embodiment, images of the first eye 160 and the second eye 260 are concurrently captured during the exposing discussed herein. FIGS. 11-12 show images of the first eye 160 and the second eye 260, respectively, each including a pupil 162, 262 having a center point 166, 266. Further, image of the first eye 160 and image of the second eye 260 can each include a pupil portion 168, 268, containing pupils 162, 262, respectively. Using image of the first eye 160 as an example, in determining center point 166 computer system 42 can convert image of the first eye 160 to a binarized image 170 (FIG. 13) that separates the pupil portion 178, from a non-pupil portion 174. As used herein, the term "binarized" means image data in which each pixel can have one of only two values. In the example of FIG. 13, the pupil portion 178 has one value (represented by black), while the non-pupil portion 174 has another value (represented by white). Binarized image 170 can be created using a histogram-based threshold operation, e.g., the Isodata algorithm. Binarized image 170 can be scanned, and using, for example, a particle analysis algorithm, computer system 42 can find edge 179 of pupil portion 174. Computer system 42 can measure edge 179 of pupil portion 174 and generate a best-fit ellipse 180 (shown in FIG. 14) using those measurements. Further, computer system 42 can scan the best-fit ellipse 180 to determine a center point 166 (FIG. 11), and divide the image of the first eye 160 into a first half 110 and a second half 120 along a line of pixels intersecting the center point 166. Further, computer system 42 can similarly divide the image of second eye 260 into a first half 210 and a second half 220.

Figure 15:
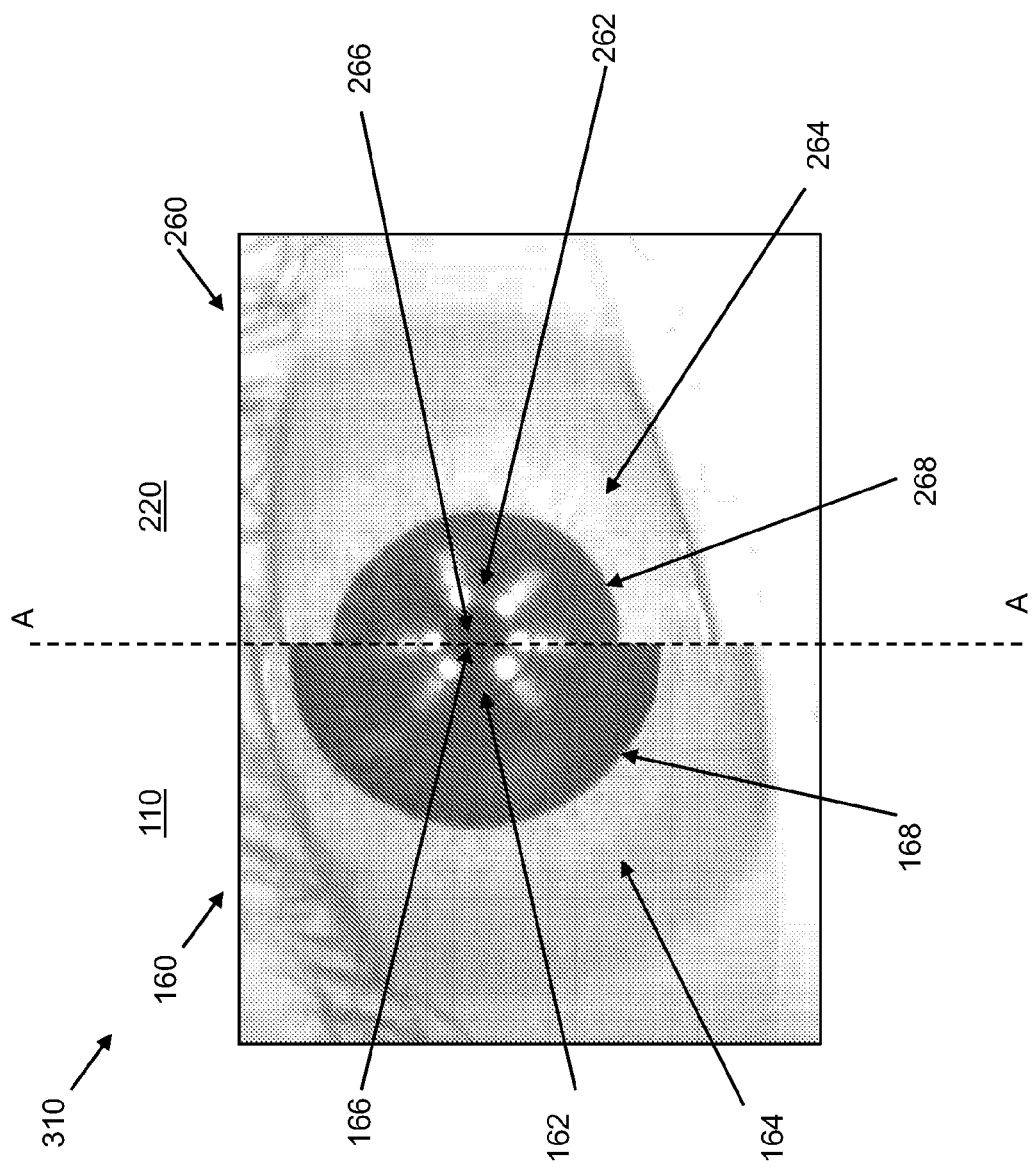
FIG. 15 shows a composite image of two eyes according to aspects of the invention.

FIG. 15 shows a composite image 310 including a first half 110 of the first eye 160 and a second half 220 of the second eye 260. As discussed herein, computer system 42 can create a binarized image, and perform edge detection to determine the edge of the pupil on each eye. Computer system 42 can perform ellipse fitting, Hough transformation, or the like to identify the center point 166 and diameter. Computer system 42 can use the corresponding portion of the image of each eye starting from the pupil centerline A-A and superimpose the two portions into a single image 310 using any solution. Computer system 42 can also vertically align the two portions using the center points 166, 266.

Figure 16A:
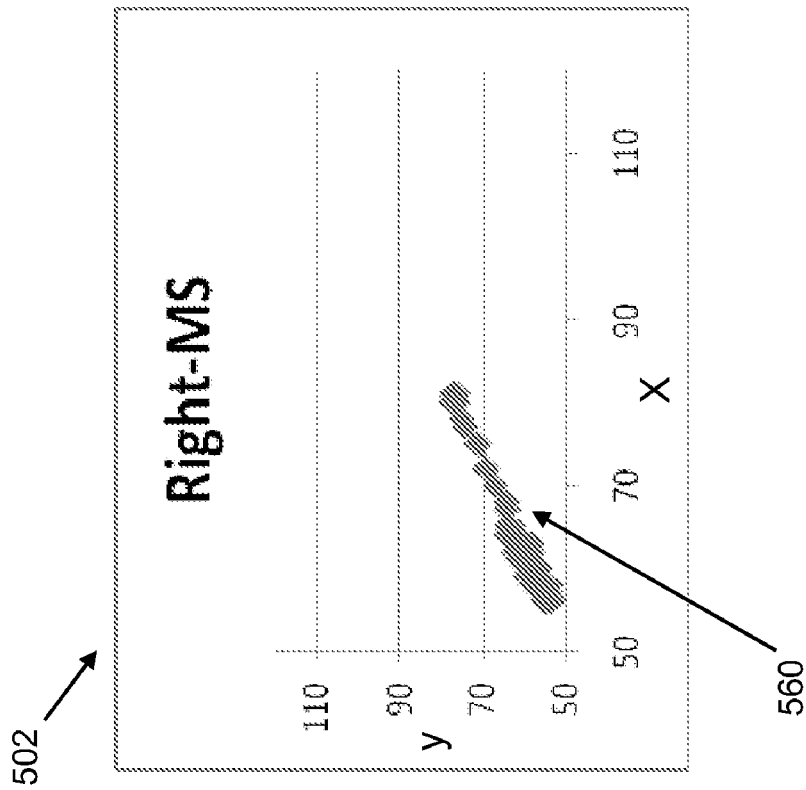
FIGS. 16A-B show graphs depicting an afferent defect of a patient.
Figure 16B:
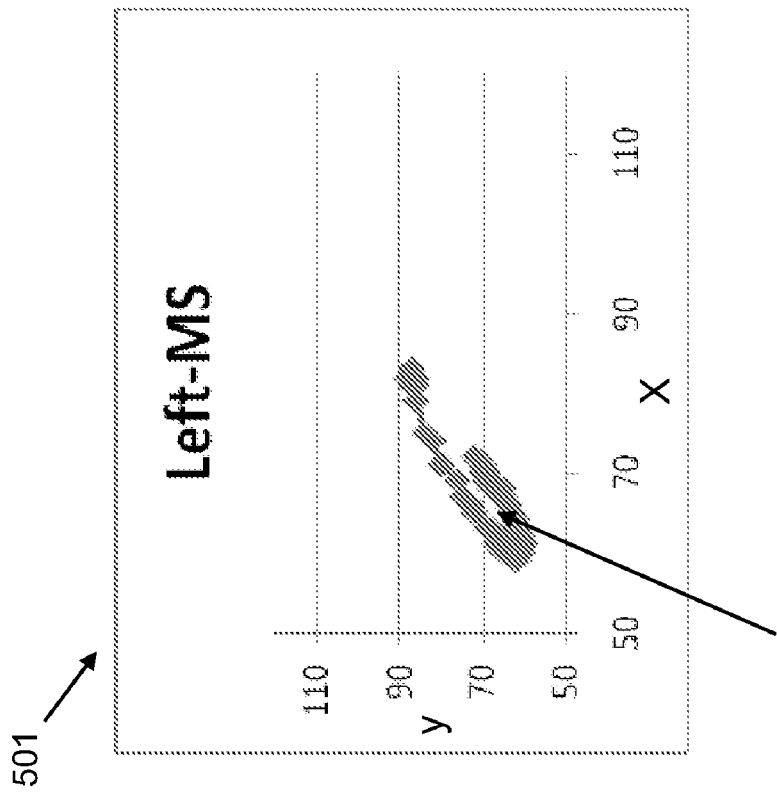

Further computer system 42 can generate an output graph whose shape can suggest a type of defect, if any. For example, computer system 42 can generate the output graph using parametric or Lissajous curves to visualize asynchrony in the pupil reflexes of the two eyes. FIGS. 16A-B show illustrative parametric output graphs 501, 502 of an MS patient. Graph 501 shows the direct (x-axis) versus consensual (y-axis) response of a patient's left eye to light stimuli in arbitrary units. Graph 502 shows the direct (x-axis) versus consensual (y-axis) response of a patient's right eye to light stimuli in arbitrary units. Unit measurements indicated on the x-axis and y-axis are arbitrary but consistent between graph 501 and graph 502. The defect in the patient's left eye is indicated by the curved shape of the data output in graph 501, which creates a "space" 550 between data points. In contrast to the relatively straight line of data 560 of graph 502, space 550 of graph 502 indicates a difference in the latency period between the left and right eye, which suggests an afferent defect in the left eye. While FIGS. 16A-B show parametric output graphs with static data, computer system 42 can plot the graph as an animation, e.g., adding each point one at a time. Computer system 42 can aid an operator in visualizing a direction of the difference by plotting the graph in this manner, which can give an indication of which eye is more defective.

Figure 17:
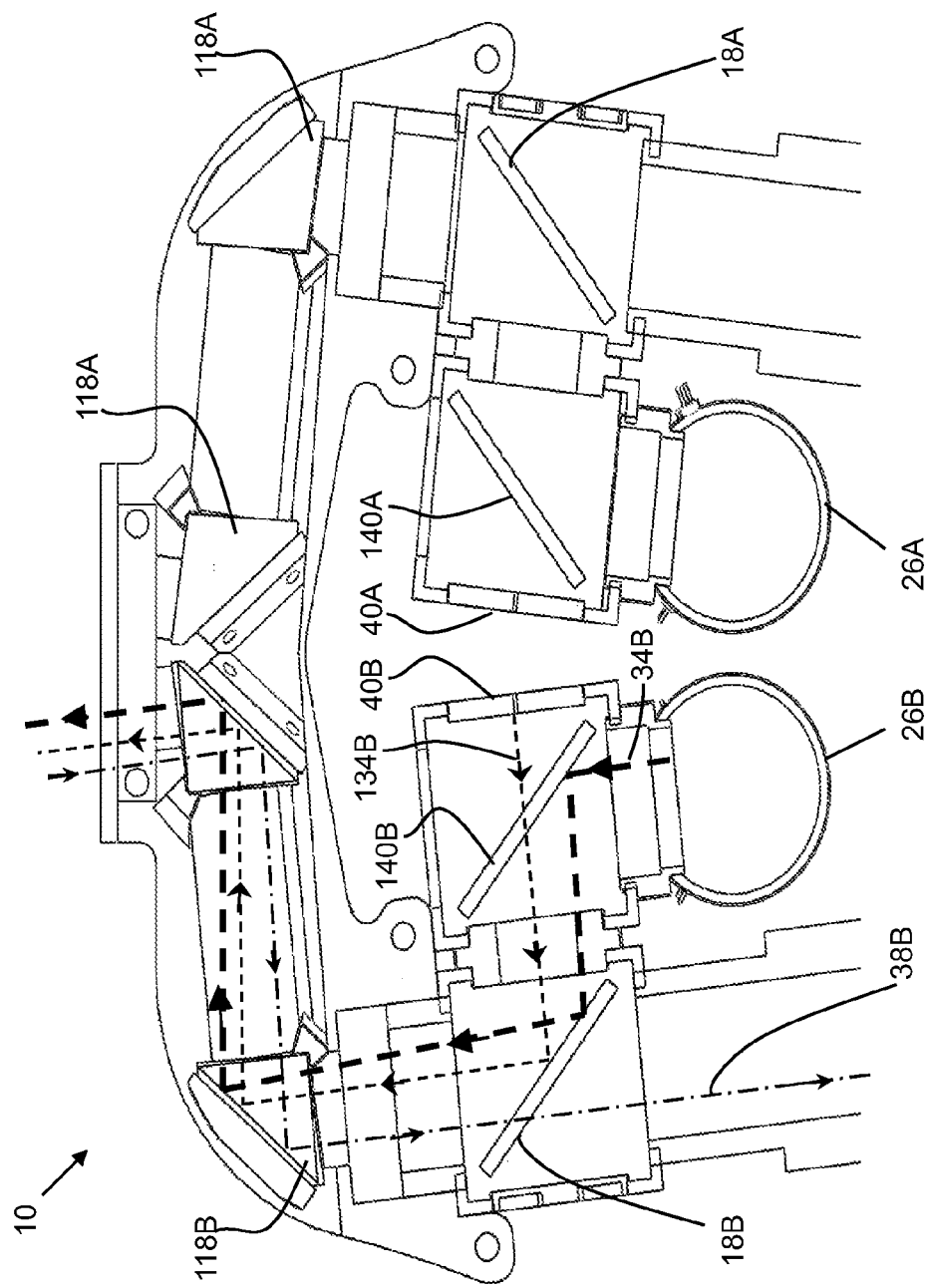
FIG. 17 shows a portion of an illustrative device according to one aspect of the invention.

An embodiment of device 10 can be portable. For example, FIG. 17 shows a top cross-sectional view of a portion of a portable version of device 10 according to an embodiment. Portable version of device 10 can include light sources 26A-B, fixation points 40A-B, beam splitter mirrors 140A-B, cold mirrors 18A-B, right-angle prisms 118A-B, infrared light sources, and recording mechanisms. Only one side of device 10 is shown in functional mode (side "B"), however, it is understood that the opposing side will function substantially similarly. Portable version of device 10 can function substantially similarly to device 10 described with reference to FIGS. 1A-1B. That is, light sources can emit beam of light 34B, which is reflected at a right angle by beam splitter mirrors 140B. Beam of light 34B can then reflect off of cold mirror 18B, which allows passing of infrared path 38B, but reflects beam of light 34B. Beam of light 34B then reflects off of right-angle prisms 118B to reach an eye of an individual. Fixation point 40B can function substantially similarly to fixation points 40A-B of FIG. 1, and can provide a central point on which the patient should focus while looking into the eye scopes. Beam splitter mirror 140B can allow passing of focal beam 134B while reflecting beam of light 34B. During testing, passage of infrared beam 38B to the eye can occur substantially as described with reference to FIG. 1B. Cold mirror 18B can allow for passage of infrared beam 38B to a recording mechanism.

As described herein, computer system 42 can implement eye tracking processes to reduce differences in the results of different pupil evaluations, which can occur due to different operators, movement by the patient, or the like. Additionally, by implementing pupil segmentation algorithm/software product in computer system 42, the portable device 10 can be made less sensitive to environmental changes, movement by the patient, and/or the like. Device 10 also can include rubber eye guards and/or adjustable inter-ocular distance pieces, such as found on stereo microscope equipment, to block ambient light and make the device more comfortable for the patient. Still further, device 10 can include eye lid retraction features, such as automatic soft-tissue retractors, for evaluating unconscious/injured subjects.

After conducting stimulation process, computer system 42 can use the results and/or assist a clinician in identifying one or more clinical categories of the patient based on the presence, absence, and/or attributes of RAPD present in the individual. Any clinical category for which RAPD is symptomatic can be identified. In an embodiment, the results can be evaluated to identify whether the patient has incurred a traumatic brain injury (TBI). Unlike a neuro-degeneration classification, TBI is a result of an injury, not disease, and is more likely to cause efferent lesions. However, both are similar in that they can interfere with neural conduction pathways of the eyes. Efferent defect information also can be able to detect other conditions, such as Horner's Syndrome.

Device 10 can be utilized in an environment, such as at a MASH unit or an emergency room, in which individuals that may have suffered TBI or an ocular injury are likely to seek care. In this case, device 10 can be used by healthcare providers to properly test standardized pupil responses, allowing the pupil responses to be periodically quantified and documented in the clinical record. Such monitoring can help avert potentially fatal consequences of increasing intracranial pressure that can accompany evolving cerebral edema or subdural hematoma, subarachnoid hemorrhage induced cerebral vasospasm and ischemia. In situations where ocular motility deficits have been previously elicited, the periodic monitoring of the progression or recovery of those might also help direct timely intervention and proper management of patients, such as injured soldiers. Early detection of potential TBI will allow for more effective treatment especially in those cases where cognitive and/or behavioral symptoms do not manifest, or are not easily recognized. Device 10 can provide quantitative, automated, and standardized pupillary function, which can assist in correctly identifying TBI, especially where expert neurologists are not available.

It is understood that the invention can be realized in hardware, software, or a combination of hardware and software. Any kind of computer/server system(s)—or other apparatus adapted for carrying out the methods described herein—is suited. A typical combination of hardware and software could be a general-purpose computer system with a computer program that, when loaded and executed, carries out the respective methods described herein. Alternatively, a specific use computer, containing specialized hardware for carrying out one or more of the functional tasks of the invention, could be utilized. The invention can also be embedded in a computer program product, which comprises all the respective features enabling the implementation of the methods described herein, and which—when loaded in a computer system—is able to carry out these methods. Computer program, software program, program, or software, in the present context mean any expression, in any language, code or notation, of a set of instructions intended to cause a system having an information processing capability to perform a particular function either directly or after either or both of the following: (a) conversion to another language, code or notation; and/or (b) reproduction in a different material form.

The foregoing description of various aspects of the invention has been presented for purposes of illustration and description. It is not intended to be exhaustive or to limit the invention to the precise form disclosed, and obviously, many modifications and variations are possible. Such modifications and variations that can be apparent to a person skilled in the art are intended to be included within the scope of the invention as defined by the accompanying claims.

What is claimed is:

1. A method of evaluating the pupillary responses of a patient, the method comprising:
   alternately exposing a first eye and a second eye of the patient to light stimulation in successive intervals, the light stimulation provided by at least one light source controlled by at least one computing device;
   concurrently capturing, with at least one image device controlled by the at least one computing device, image data of the first eye and the second eye during the exposing; and
   using the at least one computing device to perform the following:
      determine a center point of the first eye within the image data of the first eye and a center point of the second eye within the image data of the second eye;
      obtain image data of a first half of the first eye having an edge defined by a line of pixels intersecting the determined center point of the first eye;
      obtain image data of a second half of a second eye, the second half of the second eye opposing the first half of the first eye and having an edge defined by a line of pixels intersecting the determined center point of the second eye;

create a composite image including the image data of the first half of the first eye and the image data of the second half of the second eye; and provide the composite image for evaluation.

2. The method of claim 1, wherein a portion of the image data of the first half of the first eye and a portion of the image data of the second half of the second eye are superimposed in the composite image.

3. The method of claim 1, wherein the image data of the first eye includes a pupil portion and a non-pupil portion, and wherein the image data of the second eye includes an pupil portion and a non-pupil portion, wherein the obtaining includes:

convert the image data of the first eye and the second eye to binarized images of the first eye and the second eye that separate the pupil portions from the non-pupil portions;

scan the binarized image of the first eye and the second eye, using a particle analysis algorithm, to find edges of the pupil portions;

measure the edges of the pupil portions; and generate a best-fit ellipse image of each of the first eye and the second eye using the edge measurements.

4. The method of claim 1, wherein the stimulation includes white light for each exposing.

5. The method of claim 1, wherein each successive interval includes a lower-intensity stimulation than a previous interval.

6. The method of claim 5, further comprising using the at least one computing device to determine a response of the first eye and the second eye, wherein the alternately exposing in successive intervals continues until the response of the first eye is equal to the response of the second eye.

7. The method of claim 1, further comprising using the at least one computing device to perform the following:

create a succession of composite images, each of the succession of composite images corresponding to one of the successive intervals; and display the succession of composite images in time expansion.

8. A system for evaluating the pupillary responses of a patient, the system comprising:

at least one light source for alternately exposing a first eye and a second eye, respectively, to light stimulation in successive intervals;

at least one image capturing device for concurrently capturing image data of the first eye and the second eye, respectively;

an image manipulation system including:

a component configured to determine a center point of the first eye within the image data of the first eye and a center point of the second eye within the image data of the second eye;

a component configured to obtain image data of a first half of the first eye having an edge defined by a line of pixels intersecting the determined center point of the first eye;

a component configured to obtain image data of a second half of the second eye, the second half of the second eye opposing the first half of the first eye and having an edge defined by a line of pixels intersecting the determined center point of the second eye;

a component configured to create a composite image including the image data of the first half of the first eye and the image data of the second half of the second eye; and a component configured to provide the composite image for evaluation.

9. The system of claim 8, wherein the component configured to create the composite image superimposes a portion of the image data of the first half of the first eye and a portion of the image data of the second half of the second eye.

10. The system of claim 8, wherein the image data of the first eye includes an pupil portion and a non-pupil portion, and wherein the image data of the second eye includes an pupil portion and a non-pupil portion; and wherein the image manipulation system includes:

a component configured to convert the image data of the first eye and the second eye to binarized images of the first eye and the second eye that separate the pupil portions from the non-pupil portions;

a component configured to scan the binarized image of the first eye and the second eye, using a particle analysis algorithm, to find edges of the pupil portions;

a component configured to measure the edges of the pupil portions; and a component configured to generate a best-fit ellipse image of each of the first eye and the second eye using the edge measurements.

11. The system of claim 8, wherein the stimulation includes white light for each exposing.

12. The system of claim 8, wherein each successive interval includes a lower-intensity stimulation than a previous interval.

13. The system of claim 12, further comprising using the image manipulation system to determine a response of the first eye and the second eye, wherein the alternately exposing in successive intervals continues until the response of the first eye is equal to the response of the second eye.

14. The system of claim 8, wherein the component configured to create a composite image creates a succession of composite images, each of the succession of composite images corresponding to one of the successive intervals; and wherein the display displays the succession of composite images in time expansion.

15. A method of evaluating the pupillary responses of a patient, the method comprising:

alternately exposing a first eye and a second eye of the patient to light stimulation in successive intervals, the light stimulation provided by light sources controlled by at least one computing device;

concurrently capturing, with an image device controlled by the at least one computing device, image data of the first eye and the second eye during the exposing; and using the at least one computing device to perform the following:

convert the image data of the first eye and the second eye to binarized images of the first eye and the second eye that separate an pupil portion from a non-pupil portion;

determine a center point of the first eye within the image data of the first eye and a center point of the second eye within the image data of the second eye;

obtain image data of a first half of the first eye having an edge defined by a line of pixels intersecting the determined center point of the first eye;

obtain image data of a second half of a second eye, the second half of the second eye opposing the first half of the first eye and having an edge defined by a line of pixels intersecting the determined center point of the second eye;

create a composite image including the image data of the first half of the first eye and the image data of the second half of the second eye; and provide the composite image for evaluation.

16. The method of claim 15, wherein a portion of the image data of the first half of the first eye and a portion of the image data of the second half of the second eye are superimposed in the composite image.

17. The method of claim 15, further comprising using the at least one computing device to perform the following:

scan the binarized image, using a particle analysis algorithm, to find edges of the pupil portion;

measure the edges of the pupil portion; and generate a best-fit ellipse image using the edge measurements.

18. The method of claim 15, wherein each successive interval includes a lower-intensity stimulation than a previous interval.

19. The method of claim 18, further comprising using the at least one computing device to perform the following:

create a succession of composite images, each of the succession of composite images belonging to a successive interval; and display the succession of composite images in time expansion.

20. The method of claim 15, wherein the stimulation includes white light for each exposing.

* * * * *